(12) United States Patent
Lenox et al.

(10) Patent No.: US 6,900,203 B2
(45) Date of Patent: May 31, 2005

(54) OPTICALLY ACTIVE FLUORINATED VASOCONSTRICTORS, METHODS FOR MAKING THEM, AND ANESTHETIC FORMULATIONS COMPRISING THEM

(75) Inventors: Hamilton J. Lenox, Chicago, IL (US); Elena Terentieva, Hoffman Estates, IL (US); Mikhail Y. Gololobov, Hoffman Estates, IL (US)

(73) Assignee: Polium Technologies, Inc., Hoffman Estates, IL (US)

( * ) Notice: Subject to any disclaimer, the term of this patent is extended or adjusted under 35 U.S.C. 154(b) by 236 days.

(21) Appl. No.: 10/190,856

(22) Filed: Jul. 8, 2002

(65) Prior Publication Data

US 2004/0002549 A1 Jan. 1, 2004

Related U.S. Application Data

(60) Provisional application No. 60/389,839, filed on Jun. 19, 2002.

(51) Int. Cl.$^7$ .................... A61K 31/535; A61K 31/445; A61K 31/24; A61K 31/16; A61K 31/135
(52) U.S. Cl. .................... 514/229; 514/239.2; 514/330; 514/537; 514/626; 514/653; 564/362; 564/364; 564/365
(58) Field of Search ............................. 568/362, 364; 568/365; 514/626, 653, 537, 239.2, 229, 330

(56) References Cited

U.S. PATENT DOCUMENTS

| | | | |
|---|---|---|---|
| 3,845,770 A | 11/1974 | Theeuwes et al. | 128/260 |
| 4,326,525 A | 4/1982 | Swanson et al. | 128/260 |
| 4,992,445 A | 2/1991 | Lawter et al. | 514/279 |
| 5,023,252 A | 6/1991 | Hseih | 514/183 |
| 5,719,197 A | 2/1998 | Kanios et al. | 514/772.6 |

OTHER PUBLICATIONS

Kirk et al., "Synthesis and Biological Properties of 2–, 5–, and 6–Fluoronorepinephrines," *J. Med. Chem* 1979, 22, 1493–1497.

Kirk, "Fluorine–Substituted Neuroactive Amines," In *Selective Fluorination in Organic and Bioorganic Chemistry* (Welch, J.T. ed) ACS Symposium Series 456, American Chemical Society: Washington, D.C., 1991, pp. 136–155.

Jastak et al., "Vasoconstrictors and local anesthesia: a review and rationale for use," *J. Am. Dent. Assoc.* 1983, 107, 623–630.

Markovich et al., "Synthesis of Halogenated Trimetoquinol Derivatives and Evaluation of Their β–Agonist and Thromboxane A$_2$ (TXA$_2$) Antagonist Activities," *J. Med. Chem.* 1992, 35, 466–479.

Brown et al., "Solubility of Hydrogen Chloride at Low Temperatures. A Measure of the Basic Properties of Aromatic Nuclei; –and σ– Complexes and Their Role in Aromatic Substitution, " *J. Am. Chem. Soc.* 1952, 74, 3570–3576.

Arasaratnam, et al., "Reversibly soluble biocatalyst: optimization of trypsin coupling to Eudragit S–100 and biocatalyst activity in soluble and precipitated forms," *Enz. Microb. Technol.* 2000, 27, 254–263.

Effenberger et al., "Stereoselective synthesis of thienyl and furyl analogues of ephedrine," *Tetrahedron: Asymmetry,* (1997) 8, 469–476.

Effenberger et al., "Synthesis of the Adrenergic Bronchodilators (R)–Terbutaline and (R)–Salbutamol from (R)–Cyanohydrins," *J. Org. Chem.* 1997, 62, 3867–3873.

Kiljunen et al., "(R)– and (S)–Cyanohydrins Using Oxynitrilases in Whole Cells," *Tetrahedron: Asymmetry* 1996, 7, 1105–1116.

Zandbergen et al., "Synthesis of Optically Active Cyanohydrins Using Almond Meal," *Synth. Commun.* 1991, 21, 1387–1391.

Smithskamp–Wilms et al., "Hydroxynitrile lyases from almond and sorghum as biocatalysts," *Rec. Trav. Chim. Pays–Bas* 1991, 110, 209–215.

Becker et al., "Zur Kenntnis der Cyanhydrinsynthese II," *Biochem. Z.* 1963, 337, 156–166.

(Continued)

*Primary Examiner*—Peter O'Sullivan
(74) *Attorney, Agent, or Firm*—McAndrews, Held & Malloy

(57) ABSTRACT

(R)-6F-phenylephrine, essentially free of (S)-6F-phenylephrine, and an anesthetic formulation comprising (R)-6F-epinephrin or (R)-6F-phenylephrine and having improved stability compared to formulations containing their non-fluorinated analog, are disclosed. Further disclosed is a method of providing vasoconstriction in a mammal by administering the anesthetic formulation. The anesthetic composition can include an anesthetic, an (R)-chiral compound having the structure:

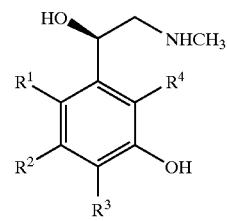

wherein $R^1$, $R^2$, and $R^4$ are independently selected from —H or —F, at least one of $R^1$, $R^2$, and $R^4$ is —F, and $R^3$ is selected from —OH, —H or —F, or a pharmaceutically acceptable salt or ester thereof, said vasoconstrictor being essentially free of the (S)-chiral form. Also, a method of chiral addition of cyanide to a ring-fluorinated phenaldehyde, employing an almond hydroxynitrile lyase enzyme, provided in the form of a reversibly soluble polymer conjugate ((R)-Finezyme™-H series biocatalysts) is disclosed. Several such biocatalysts are disclosed.

7 Claims, 13 Drawing Sheets

OTHER PUBLICATIONS

Franz Effenberger, "Hydroxynitrile Lyases in Stereoselective Synthesis," *Stereoselective Biocatalysis,* (Patel, R.N., ed.), Marcel Dekker, 2000, pp. 321–342.

Brussee et al., "Biocatalysis in the Enantioselective Formation of Chiral Cyanohydrins, Valuable Building Block in Organic Synthesis," *Stereoselective Biocatalysis* (Patel, R.N., ed.), Marcel Dekker, 2000, pp. 289–320.

Schmidt et al., "Oxynitrilases: From Cyanogenesis to Asymmetric Synthesis," *Biocatalysis—From Discovery to Application* (Fessner, W.D., ed.), Springer, 1999, pp. 193–226.

Effenberger et al., "(R)–Oxynitrilase Catalyzed Synthesis of (R)–Ketone Cyanohydrins," *Tetrahedron: Asymmetry* 1995, 6, 2945–2952.

Effenberger et al. "Enzyme–catalyzed Synthesis of (R) Ketone–Cyanhohydrins and Their Hydrolysis to (R) α–Hydroxy–α–Methyl–Carboxylic Acids," *Tetrahedron Lett.* 1991, 32, 2605–2608.

Warmerdam et al., "Synthesis of (R)– and (S)–2–hydroxy–3–enoic acid esters," *Recl. Trav. Chim. Pays–Bas* 1996, 115, 20–24.

Huuhtanen et al., "Enzyme–Catalysed Synthesis of Optically Active Aliphatic Cyanohydrins," *Tetrahedron: Asymmetry* 1992, 3, 1223–1226.

Belokon et al., "Asymmetric addition of trimethylsilyl cyanide to aldehydes catalysed by chiral (salen)Ti$^{IV}$ complexes," *Chem. Soc., Perkin Trans. I* 1997, 1293–1295.

Adejare et al., "Syntheses and Adrenergic Activities of Ring–Fluorinated Epinephrines," *J. Med. Chem.* 1988, 31, 1972–1977.

Meier et al., "[abc]–Annealated [18]Annulenes," *J. Org. Chem.* 1992, 57, 6847–6852.

Kirk et al., "Synthesis and Adrenergic Activity of Ring–Fluorinated Phenylephrines," *J. Med. Chem.* 1986, 29, 1982–1988.

Lu et al., "Syntheses of (R)– and (S)–2– and 6–Fluoronorepinephrine and (R)– and (S)–2– and 6–Fluoroepinephrine: Effect of Stereochemistry on Fluorine–Induced Adrenergic Selectives," *J. Med. Chem.* 2000, 43, 1611–1619.

Daniel Venter, "The Acid–catalysed Racemisation Mechanism of Catecholamines," *Tetrahedron* 1991, 47, 5019–5024.

Madden et al., "The Range of Medication Storage Temperatures In Aeromedical Emergency Medical Services," *Prehospital Emergency Care* 1999, 3, 27–30.

Schmidt et al., "Preparation of Optically Active Cyanohydrins Using the (S)–Hydroxynitrile Lyas from *Hevea brasiliensis,*" *Tetrahedron* 1996, 52, 7833–7840.

Hondrom, S. O.; Seng, G. E.; Rebert, N. W. *Anesthesia and Pain Control in Dentistry* 1993, 2, 198–202.

Cancañón, F.; Paulus, B. F.; Thompson, g. A.; Ammann, J. R. Investigation of Vasoconstrictor Degradation in Local Anesthetic Injections 30th Annual Meeting & Exhibition of the AADR and 25th Annual Meeting of the CADR, Chicago, 2001.

Gregory, R. J. H. *Chem. Rev.* 1999, 99, 3649–3682.

Furlano, D.; Kirk, K. K. *J. Org. Chem.* 1986, 51, 4073–4075.

Remington's Pharmaceutical Sciences, Mace Publishing Co., Philadelphia, Pa. 17th Ed. (1985) and "Modern Pharmaceutics," Marcel Dekker, Inc. 3.sup.rd Ed. (G. S. Banker & C. T. Rhodes, Eds.) (copy not enclosed).

J. March, Advanced Organic Chemistry: Reactions, Mechanisms and Structure, 4th Ed. (New York: Wiley–Interscience, 1992).

P. J. Kuzma et al, Regional Anesthesia 22 (6): 543–551 (1997).

LIDOCAINE (R)-(-)-EPINEPHRINE (R)-PHENYLEPHRINE (S)-PHENYLEPHRINE (R)-2F-PHENYLEPHRINE (S)-2F-PHENYLEPHRINE (R)-6F-PHENYLEPHRINE (S)-6F-PHENYLEPHRINE

OPTICALLY ACTIVE FLUORINATED VASOCONSTRICTORS, METHODS FOR MAKING THEM, AND ANESTHETIC FORMULATIONS COMPRISING THEM

CROSS-REFERENCE TO RELATED APPLICATIONS

Priority is claimed from provisional application Ser. No. 60/389,839, filed Jun. 19, 2002, by Hamilton J. Lenox, Elena Terentieva and Mikhail Y. Gololobov, now pending. The entire specification and all the claims of the provisional application referred to above are hereby incorporated by reference to provide continuity of disclosure.

This work was funded, in part, by The National Institutes of Health, Grant No. 1R43 GM 60830-01 awarded by the National Institute of General Medical Sciences.

BACKGROUND

This application relates generally to optically active fluorinated vasoconstrictors, methods and reversibly soluble enzymes employed for making them, and anesthetic formulations comprising them. One typical use for a vasoconstrictor is as an ingredient of a local anesthetic composition.

Typical local anesthetic injections are composed of the following ingredients:

Lidocaine hydrochloride (anesthetic, FIG. 1)

(R)-(−)-Epinephrine bitartrate (vasoconstrictor, FIG. 2. The vasoconstrictor impedes systemic absorption, increases duration of anesthesia, and allows rate of drug metabolism to equal rate of drug absorption.)

Sodium or potassium metabisulfite (antioxidant)

Sodium chloride to achieve isotonicity

EDTA or citric acid (chelating agents)

Water (solvent; pH is adjusted to 3.3–5.5 with HCl or NaOH)

Minor impurities such as aluminum salts

Local anesthetics employed for dental and medical applications are ubiquitous pharmaceuticals in the private sector and military. Jastak, J. T.; Yagiela, J. A. *J. Am. Dent. Assoc.* 1983, 107, 623–630. Current formulations work well in hospitals, but quickly lose their efficacy during transport and storage in field austere environments where climate control may not be available. Hondrum, S. O.; Seng, G. E.; Rebert, N. W. *Anesthesia and Pain Control in Dentistry* 1993, 2, 198–202. Madden, J. F.; O'Connor, R. E.; Evens, J. *Prehospital Emergency Care* 1999, 3, 27–30. Thus, it is important to develop new thermo- and photo-stable local anesthetic formulations. Although lidocaine is relatively stable to harsh environmental conditions, previous investigations suggest a correlation between the loss of efficacy of anesthetic injections and decomposition of the contained vasoconstrictor. Hondrum, S. O.; Seng, G. E.; Rebert, N. W. *Anesthesia and Pain Control in Dentistry* 1993, 2, 198–202. Madden, J. F.; O'Connor, R. E.; Evens, J. *Prehospital Emergency Care* 1999, 3, 27–30.

New vasoconstrictors should adhere to four main criteria:

1) Resist acid-catalyzed racemization

2) Experience little or no photochemical destruction

3) Exhibit α-adrenergic properties similar to epinephrine, with minimal β-adrenergic activity 4) Retard the rate of systemic absorption of the anesthetic Mechanism of Racemization of Aminophenylethanols Evidence suggests that a major pathway for destruction of 2-methylamino-1R-hydroxy-phenylethanols is racemization. While the role of light in this process is not fully understood, the key step of acid-catalyzed elimination of the OH-group at the chiral center is without doubt (Table 1 and FIG. 3). Venter, D. P. *Tetrahedron* 1991, 47, 5019–5024. From the data in Table 1, it is clear that p-hydroxy aminophenylethanols racemize markedly faster than compounds possessing p-methoxy-groups, and those without p-substituents are practically unreactive toward racemization in acid media. The simplest plausible mechanism to explain this data would involve a loss of the hydroxyl group at the chiral center, resulting in the formation of unstable achiral quinone intermediates. In the reverse reaction, these intermediates can form both stereoisomers at the same rates, resulting in racemization.

TABLE 1

Racemization of substituted aminophenylethanols in 1.0 M HCl at 30° C.[1.]

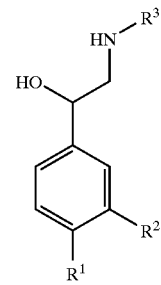

| Compound | Rate constant, (min$^{-1}$) |
|---|---|
| $R^1$ = H, $R^2$ = OH, $R^3$ = $CH_3$ | 3.2 $10^{-7}$ |
| $R^1$ = $R^2$ = H, $R^3$ = $CH(CH_3)$ | 8.4 $10^{-7}$ |
| $R^1$ = $R^2$ = $OCH_3$, $R^3$ = $CH(CH_3)$ | 1.0 $10^{-4}$ |
| $R^1$ = $OCH_3$, $R^2$ = H, $R^3$ = $CH(CH_3)$ | 1.5 $10^{-4}$ |
| $R^1$ = $R^2$ = OH, $R^3$ = $CH_3$ | 4.1 $10^{-4}$ |
| $R^1$ = $R^2$ = OH, $R^3$ = $CH(CH_3)_2$ | 4.5 $10^{-4}$ |

[1.]Venter, D. P. Tetrahedron 1991, 47, 5019–5024.

J. R. Ammann and colleagues applied this idea to the interpretation of their studies of the stability of commercial anesthetic injections. Cancañon, F.; Paulus, B. F.; Thompson, g. A.; Ammann, J. R. Investigation of Vasoconstrictor Degradation in Local Anesthetic Injections 30th Annual Meeting & Exhibition of the AADR and 25th Annual Meeting of the CADR, Chicago, 2001. Commercial injections contain (R)-epinephrine as a vasoconstrictor, along with such additives as metabisulfite and aluminum salts. These injections also are less acidic, thus the methylamino group of the vasoconstrictor remains unprotonated. FIG. 4 depicts the proposed mechanism of racemization of epinephrine through interactions with the additives in commercial anesthetic injections.

Requirements 3 and 4 (see above) impose severe limitations on the "allowed" structure variations of the epinephrine molecule. (R)-Epinephrine binding to α-adrenergic receptors is very effective, having a binding constant with respect to $α_1$-receptors on the order of 1 μM and to $α_2$-receptors on the order of 0.01 μM. Lu, S.; Herbert, B.; Haufe, G.; Laue, K. W.; Padgett, W. L.; Oshunleti, O.; Daly, J. W.; Kirk, K. L. *J. Med. Chem.* 2000, 43, 1611–1619. Binding of (R)-phenylephrine with α-receptors is also characterized by binding constants on the order of several μM. Kirk, K. L.; Olubajo, O.; Buchhold, K.; Lewandowski, G. A.; Gusowski, F.; McCulloh, D.; Daly, J. W.; Creveling, C. R. *J. Med. Chem.* 1986, 29, 1982–1988. Therefore, (R)-epinephrine and (R)-phenylephrine molecules fit precisely in the binding cavity of the receptors, and any substituents that significantly change the size of the molecule likely will disturb binding.

SUMMARY OF THE INVENTION

The present inventors have discovered that the problem of racemization, and thus a reduction in the potency, of vasoconstrictors such as epinephrine and phenylephrine, for example in local anesthetic formulations, can be addressed by ring fluorinating the vasoconstrictors. The fluorinated vasoconstrictors are more stable than the presently employed non-fluorinated analogs, while retaining utility as vasoconstrictors.

BRIEF DESCRIPTION OF DRAWING FIGURES

DETAILED DESCRIPTION OF THE INVENTION

Figure 1:
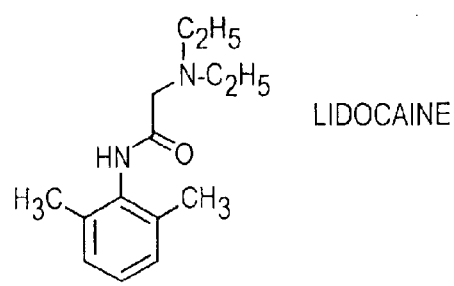
FIG. 1 is the structure of lidocaine.
Figure 2:
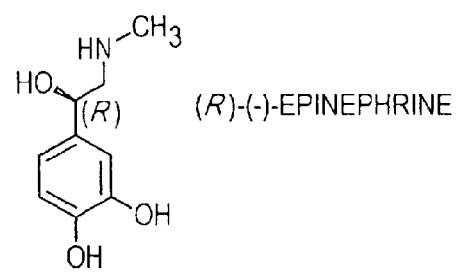
FIG. 2 is the structure of (R)-(–)-Epinephrine.
Figure 3:
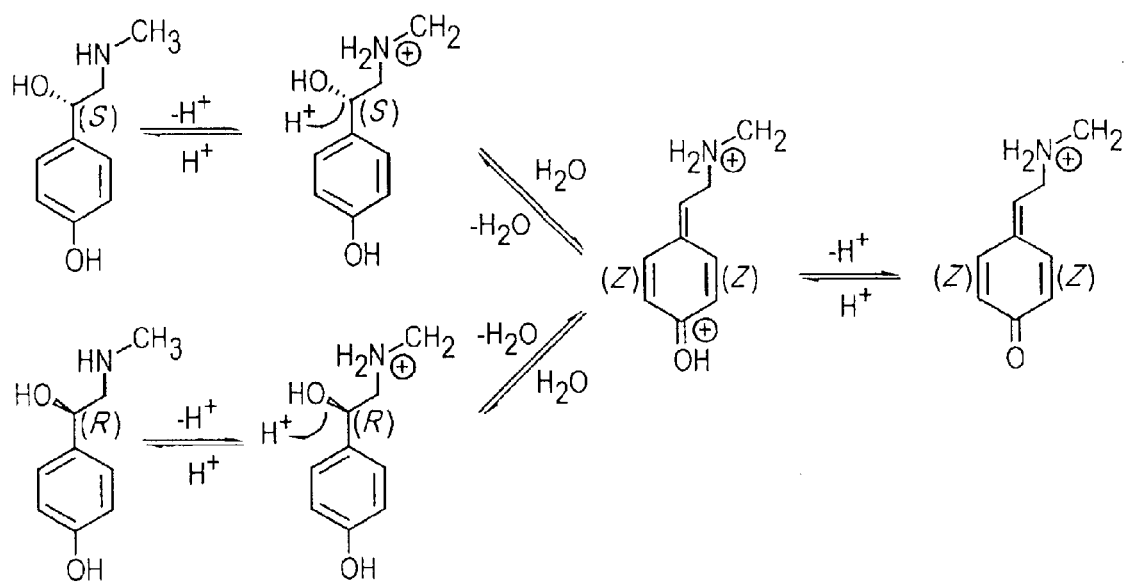
FIG. 3 is the general mechanism of racemization of 2-methylamino-1-hydroxyphenylethanols in 1.0 M HCl suggested in the literature.

The present inventors have observed that the mechanisms depicted in FIGS. 2 and 3 share one key step: elimination of the OH-group. The present inventors contemplate that any modifications of the 2-methylamino-1R-hydroxyphenylethanol molecules that hamper water elimination and formation of the quinone-like intermediate should increase the stability of the vasoconstrictor. Loss of a water molecule requires the protonation of the oxygen that converts the hydroxyl group of the alcohol into an excellent leaving group, thus modifications that increase the acidity of the alcohol OH-group should decrease the rate of racemization. Epinephrine analogs without the p-hydroxy-group [(R)-phenylephrine, 2-methylamino-1R-(3-hydroxyphenyl)ethanol] should be more stable to racemization than (R)-epinephrine, and (R)-phenylephrine derivatives with substituents increasing the acidity of the alcohol OH-group should be more stable than the original (R)-phenylephrine.

The steric restrictions imposed by Requirements 3 and 4 can be met by producing fluorinated epinephrine derivatives, which should have the least effect on binding due to the relative similarity in size of fluorine to hydrogen. The relatively small steric alterations that result from this substitution often cause no changes in the steric interactions of the analog with a variety of biological systems, such as enzyme active sites, receptor systems, and transport systems. While the altered electronic properties of the analog, and/or altered available reaction pathways can change the chemical and biological properties of the analog dramatically, these particular fluorinated compounds have utility as vasoconstrictors.

Biochemical Properties of Substituted 2-Methylaminohydroxyphenylethanols

Table 2 includes quantitative data on the binding properties of both isomers of epinephrine and its fluorinated analogs.

TABLE 2

Structure and affinity of epinephrine and its fluorinated derivatives to different receptors. Lu, S.; Herbert, B.; Haufe, G.; Laue, K. W.; Padgett, W. L.; Oshunleti, O.; Daly, J. W.; Kirk, K L.. J. Med. Chem. 2000, 43, 1611–1619.

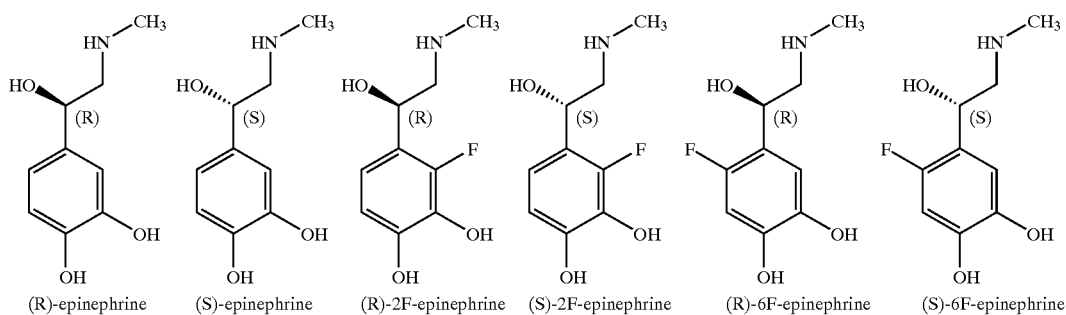

| | (R)-epinephrine | (S)-epinephrine | (R)-2F-epinephrine | (S)-2F-epinephrine | (R)-6F-epinephrine | (S)-6F-epinephrine |

Receptor affinity ($\mu$M)

| Compound | $\alpha_1$ | $\alpha_2$ | $\beta_1$ | $\beta_2$ |
|---|---|---|---|---|
| (R)- | 1.6 ± 0.2 | 0.013 ± 0.002 | 1.1 ± 0.3 | 066 ± 0.02 |

TABLE 2-continued

Structure and affinity of epinephrine and its fluorinated derivatives to different receptors. Lu, S.; Herbert, B.; Haufe, G.; Laue, K. W.; Padgett, W. L.; Oshunleti, O.; Daly, J. W.; Kirk, K L.. J. Med. Chem. 2000, 43, 1611–1619.

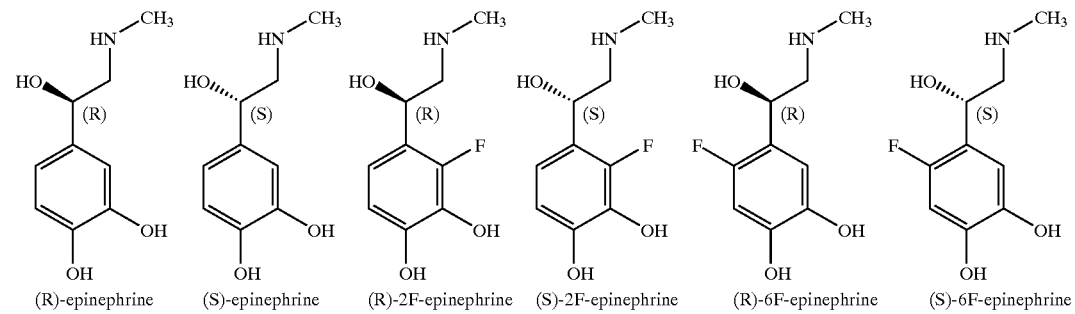

| Compound | Receptor affinity ($\mu M$) | | | |
|---|---|---|---|---|
| | $\alpha_1$ | $\alpha_2$ | $\beta_1$ | $\beta_2$ |
| epinephrine (S)-epinephrine | ~20 | 0.045 ± 0.003 | 13 ± 2 | 3.7 ± 0.5 |
| (R)-2F-epinephrine | ~25 | 0.067 ± 0.003 | 0.56 ± 0.03 | 0.11 ± 0.03 |
| (S)-2F-epinephrine | ~40 | 0.053 ± 0.001 | ~150 | ~25 |
| (R)-6F-epinephrine | 2.5 ± 0.1 | 0.013 ± 0.002 | ~100 | 38 ± 7 |
| (S)-6F-epinephrine | ~70 | 0.078 ± 0.001 | ~400 | ~90 |

Figure 4:
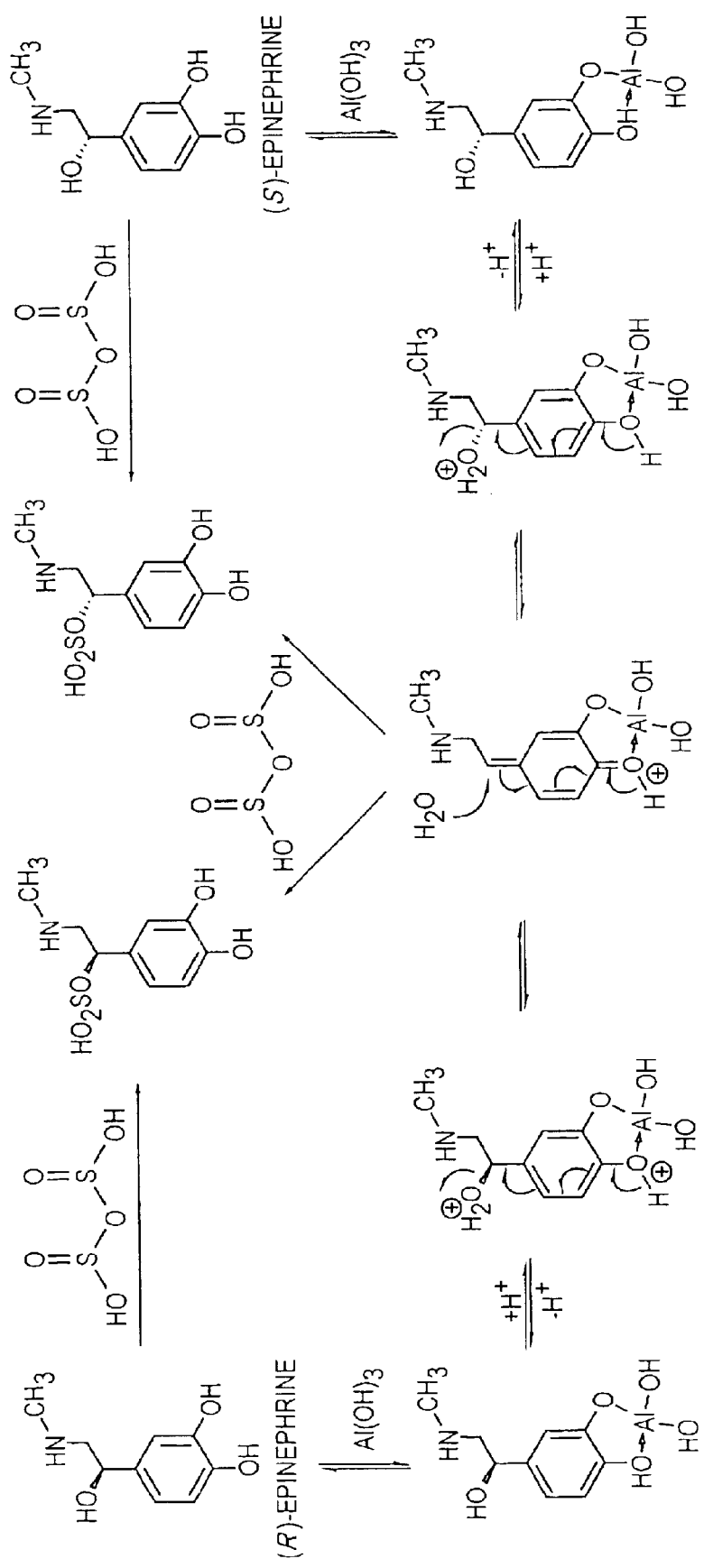
FIG. 4 depicts the proposed mechanism of racemization of epinephrine through interactions with the additives in commercial anesthetic injections.
Figure 5:
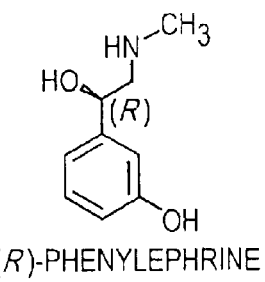
FIG. 5 shows the structure of (R)-phenylephrine.
Figure 6:
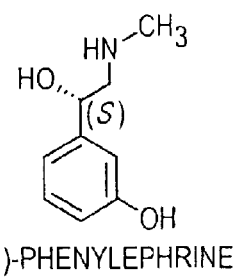
FIG. 6 shows the structure of (S)-phenylephrine.

Table 2 shows that (R)-6F-epineprine exhibits α-adrenergic properties similar to epinephrine, with minimal-adrenergic activity. While quantitative data on fluorinated derivatives of phenylephrine (FIG. 4) is not available, binding studies performed with racemic fluorinated phenylephrines show that 6F-phenylephrine is a much more selective α-adrenergic receptor agonist than (R)-phenylephrine. While (R)-phenylephrine shows an $\alpha_1/\beta$ selectivity of only about 2–5-fold and $\alpha_2/\beta$ selectivity of 33-fold, 6F-phenylephrine shows an $\alpha_1/\beta$ selectivity of 86–140-fold and an $\alpha_2/\beta$ selectivity of 780-fold. Kirk, K. L.; Olubajo, O.; Buchhold, K.; Lewandowski, G. A.; Gusowski, F.; McCulloh, D.; Daly, J. W.; Creveling, C. R. *J. Med. Chem.* 1986, 29, 1982–1988. The structures of chiral phenylephrine and its fluorinated derivatives are shown in FIGS. 5–10.

Among different possible mechanisms of fluorine-induced alteration of agonist specificities, Kirk, K. L. *In Selective Fluorination in Organic and Bioorganic Chemistry* (Welch, J. T. ed) ACS Symposium Series 456, American Chemical Society: Washington, D.C., 1991, pp. 136–155, the electrostatic repulsion model (FIG. 5) seems to be the most consistent with available data.

Figure 11:
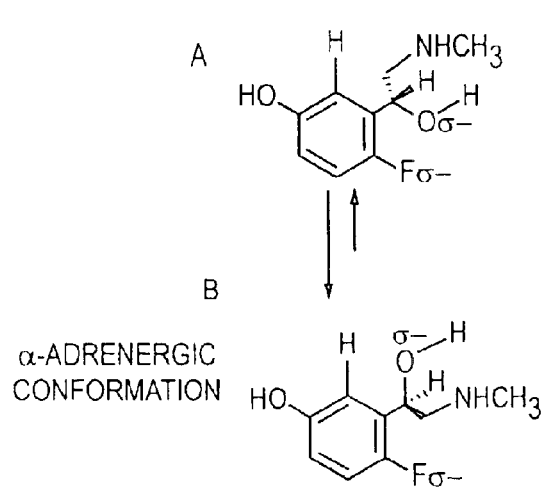
FIG. 11 shows an electrostatic repulsion model of fluorine-induced alteration of agonist specificities.
Figure 11:
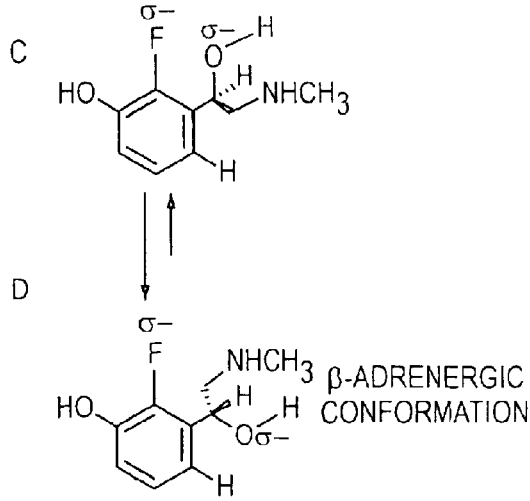

Electrostatic Repulsion Model of Fluorine-induced Alteration of Agonist Specificities Referring to FIG. 11, electrostatic repulsion should be most severe in conformations A and C. In conformations B and D, the distance between partial negative charges on the fluorine and hydroxyl oxygen atoms is the largest. This makes α-adrenergic conformation B preferable for 6-flourinated derivatives, and β-adrenergic conformation D preferable for 2-flourinated derivatives. Since the required candidate should preferentially bind to α-receptors, 6-fluorinated derivatives of (R)-epinephrine and (R)-phenylephrine are the most plausible candidates for stable vasoconstrictors.

Racemization of 6-Fluorinated Epinephrines and Phenylephrines

The electronegative nature of fluorine at the ortho-position (with respect to the aminoethanol moiety) lowers the basicity of the alcohol hydroxyl group. This should hamper both protonation of this group and water elimination. Since water elimination is a key step of the mechanisms shown in FIGS. 2 and 3, 6-fluorinated derivatives of epinephrine and phenylephrines are more stable to racemization than their non-fluorinated counterparts. However, fluorine substitution definitely increases acidity of the hydroxyl group at the 4-position. This may have negative effects on the stability of (R)-6F-epinephrine compared to (R)-6F-phenylephrine. If this is the case, (R)-6F-phenylephrine may be a better candidate for a stable vasoconstrictor.

Compound Disclosure

The novel ring-fluorinated phenylephrine vasoconstrictors of the present invention are (R)-chiral molecules represented by the general formulation:

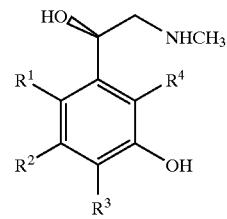

wherein $R^1$, $R^2$, $R^3$, and $R^4$ are independently selected from —H or —F, and at least one of $R^1$, $R^2$, $R^3$, and $R^4$ is —F. The chiral center in the above structure is the carbon atom attached ortho to $R^1$ and $R^4$.

The novel ring-fluorinated epinephrine vasoconstrictors of the present invention are (R)-chiral molecules represented by the same general formulation above, wherein $R^1$, $R^2$, and $R^4$ are independently selected from —H or —F, at least one of $R^1$, $R^2$, and $R^4$ is —F, and $R^3$ is —OH. The (R)-chiral molecules are biologically active as vasoconstrictors, while the (S)-chiral species are not.

These compounds may be synthesized and used substantially free from their (S)-chiral analogs. A mixture of (R)-chiral and (S)-chiral forms of a compound is regarded as "substantially free" of the (S)-chiral form, for the present purpose, if it contains at least 70% by weight of the (R)-chiral form and no more than 30% of the (S)-chiral form, based on the total weight of (R)- and (S)-chiral molecules present (i.e. at least a 70:30 weight ratio). Alternatively, a higher weight ratio of the (R)-chiral form can be provided, such as at least 75:25, alternatively at least 80:20, alternatively at least 85:15, alternatively at least 90:10, alternatively at least 95:5, alternatively at least 96:4, alternatively at least 97:3, alternatively at least 98:2, alternatively at least 99:1.

Synthesis of Ring-fluorinated Aminophenylethanols

Fluorinated epinephrine derivatives have been synthesized in both racemic and chiral forms; the synthesis of chiral fluorinated phenylephrines is believed to be new. Published methods of the synthesis of racemic and (R)-stereoisomers consist of three major steps:

1) Synthesis of fluorinated hydroxybenzaldehydes if they are not commercially available
2) Synthesis of alcohols via cyanohydrins
3) Side chain elaboration The precursor of 6F-phenylephrine, 2-fluoro-5-methoxybenzaldehyde, is commercially available (Lancaster, Fluorochem). The precursor of 6F-epinephrine, 2-fluoro-4,5-dimethoxybenzaldehyde, can be synthesized from commercially available 4-fluoroveratrole (4-fluoro-1,2-dimethoxybenzene, Aldrich, Lancaster) by formylation with 1,1-dichlorodimethyl ether. Meier, H.; Kretzschmann, H.; Kolshorn, H. *J. Org. Chem.* 1992, 57, 6847–6852. Further steps to racemic 6F-epinephrine and 6F-phenylephrine are similar for both compounds. Kirk, K. L.; Olubajo, O.; Buchhold, K.; Lewandowski, G. A.; Gusowski, F.; McCulloh, D.; Daly, J. W.; Creveling, C. R. *J. Med. Chem.* 1986, 29, 1982–1988. Kirk, K. L.; Cantacuzene, D.; Nimitkitpaisan, Y.; McCulloh, D.; Padgett, W. L.; Daly, J. W.; Creveling, C. R. *J. Med. Chem.* 1979, 22, 1493–1497. Adejare, A.; Gusovsky, F.; Padgett, W.; Creveling, C. R.; Daly, J. W.; Kirk, K. L. *J. Med. Chem.* 1988, 31, 1972–1977.

Figure 12:
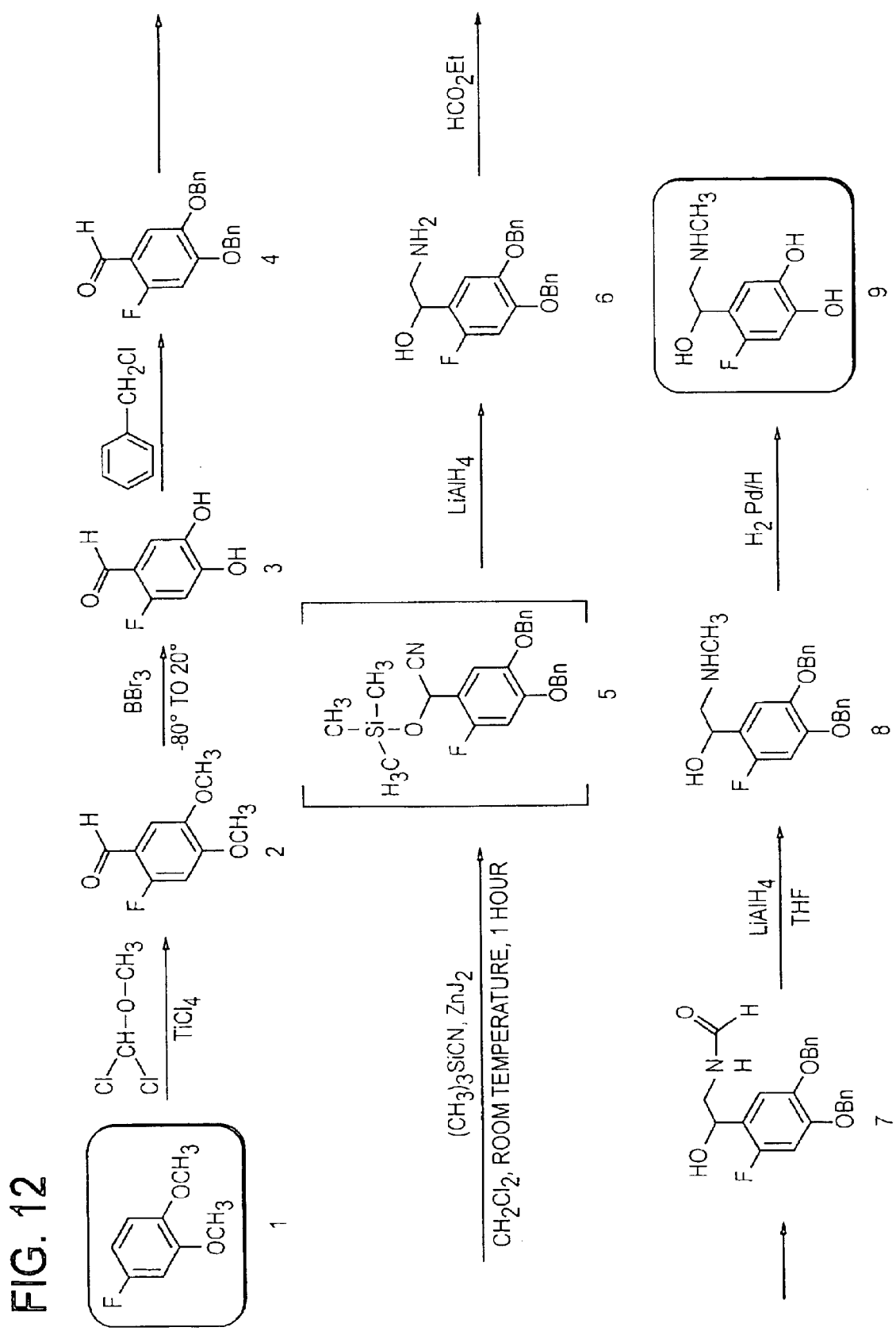
FIG. 12 shows a synthesis of racemic 6F-epinephrine.

FIG. 12 depicts the synthesis of racemic 6F-epinephrine as an example. The fluorinated aldehyde 2, synthesized by formylation of 4-fluoroveratrole (1) with 1,1-dichlorodimethyl ether, is demethylated with $BBr_3$ to fluorocatechol (3) and converted to the dibenzyl derivative 4. Direct preparation of cyanohydrins by addition of HCN under usual conditions is impossible due to the low electrophilicity of the carbonyl group of a fluorinated aldehyde. Therefore, dibenzyl fluorinated aldehyde 4 is converted to O-protected cyanohydrin 5 by the $ZnI_2$-catalyzed addition of trimethylsilyl cyanide. Cyanohydrin 5 is treated (without isolation) with $LiAlH_4$ to yield the aminoethanol derivative 6. N-Formylation of the aminoethanol derivative 6 with ethyl formate, followed by reduction, gives the final product.

Figure 7:
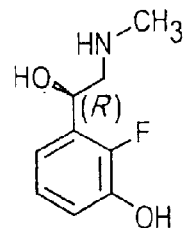
FIG. 7 shows the structure of (R)-2F-phenylephrine.
Figure 8:
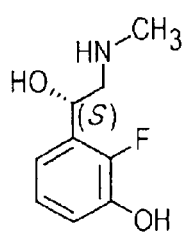
FIG. 8 shows the structure of (S)-2F-phenylephrine.
Figure 9:
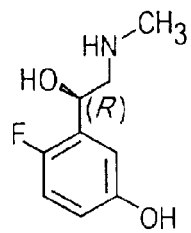
FIG. 9 shows the structure of (R)-6F-phenylephrine.
Figure 10:
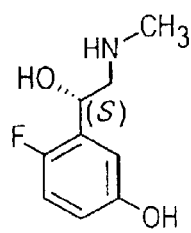
FIG. 10 shows the structure of (S)-6F-phenylephrine.

The published synthesis of chiral (R)-6F-epinephrine uses a similar reaction sequence with asymmetric cyanohydrin formation catalyzed by the (S,S)-salen catalyst (FIG. 7). Belokon', Y.; Flego, M.; Ikonnikov, N.; Moscalenko, M.; North, M.; Orizu, C.; Tararov, V.; Tasinazzo, M. *J. Chem. Soc., Perkin Trans.* 1 1997, 1293–1295.

Figure 13:
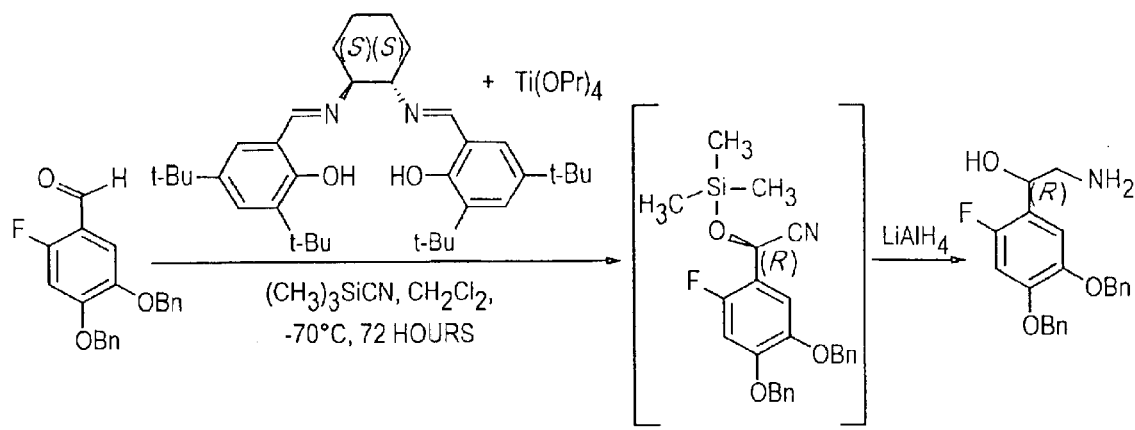
FIG. 13 shows the chiral step in the synthesis of (R)-6F-epinephrine via an asymmetric cyanohydrin route.

Chiral Step in the Synthesis of (R)-6F-Epinephrine Via Asymmetric Cyanohydrin Route FIG. 13 shows the chiral step in the synthesis of (R)-6F-epinephrine via an asymmetric cyanohydrin route. Contrary to the $ZnI_2$-catalyzed racemic cyanohydrin synthesis, the similar asymmetric step requires maintaining the reaction at −70° C. for 72 hours. This is difficult to perform even in small laboratory scale, and the scale-up requires special reactors, with much higher expense.

A similar method of asymmetric cyanohydrin formation can be used for asymmetric synthesis of (R)-6F-phenylephrine, although no literature precedent for the asymmetric synthesis of fluorinated phenylephrines was found.

Hydroxynitrile Lyase in Cyanohydrin Synthesis

The PaHNL enzyme [hydroxynitrile lyase from almonds (*Prunis amygdalis*)] catalyzes the addition of HCN to carbonyl compounds and gives products of the required (R)-configuration with excellent chemical yield and optical purity. (a) Huuhtanen, T. T.; Kanerva, L. T. *Tetrahedron: Asymmetry* 1992, 3, 1223–1226; (g) Warmerdam, E. C. J. C.; van der Nieuwendijk, A. M. C. H.; Kruse, C. G.; Brussee, J.; van der Gen, A. *Recl. Trav. Chim. Pays-Bas* 1996, 115, 20–24; (h) Effenberger, F.; Horsch, B.; Weingart, F.; Ziegler, T.; Kuhner, S. *Tetrahedron Lett.* 1991, 32, 2605–2608; (i) Effenberger, F.; Heid, S. *Tetrahedron: Asymmetry* 1995, 6, 2945–2952. (a) Schmidt, M.; Griengl, H. In *"Biocatalysis— From Discovery to Application"* (Fessner, W.-D., ed.), Springer, 1999, pp. 193–226; (b) Brussee, J.; van der Gen, A. In *"Stereoselective Biocatalysis"* (Patel, R. N., ed.), Marcel Dekker, 2000, pp. 289–320; (c) Effenberger, F. In *"Stereoselective Biocatalysis"* (Patel, R. N., ed.), Marcel Dekker, 2000, pp. 321–342. Enzymes catalyzing addition of HCN to carbonyl compounds are known under the following names: oxynitrilases, hydroxynitrile lyases and mandelonitrile lyases.

Here, we refer the enzyme from almonds *Prunis amygdalis* as PaHNL. PaHNL consists of four iso-enzymes; two iso-enzymes dominate and constitute over 90% of the PaHNL content. Becker, W.; Bentlin, U.; Eschenhof, E.; Pfeil, E. *Biochem. Z.* 1963, 337, 156–166. Smithskamp-Wilms, E., Brussee, J. & van der Gen, A. *Rec. Trav. Chim. Pays-Bas* 1991, 110, 209–215. The molecular weight of all iso-enzymes is about 57800–59000, depending on the degree of glycosylationi. The enzyme content is up to 9 g per 1 kg of dried almonds. Becker, W.; Bentlin, U.; Eschenhof, E.; Pfeil, E. *Biochem. Z.* 1963, 337, 156–166. The enzyme has been reported for use in the syntheses of many chiral cyanohydrins:

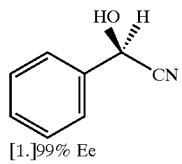

[1.] 99% Ee

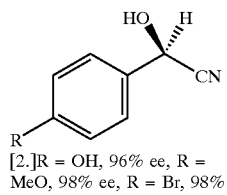

[2.] R = OH, 96% ee, R = MeO, 98% ee, R = Br, 98%

-continued

Ee

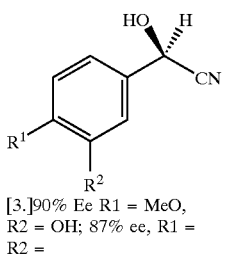

[3.] 90% Ee R1 = MeO, R2 = OH; 87% ee, R1 = R2 =

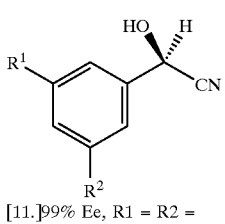

[11.] 99% Ee, R1 = R2 =

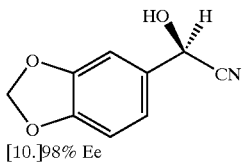

[10.] 98% Ee

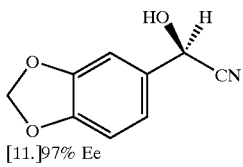

[11.] 97% Ee

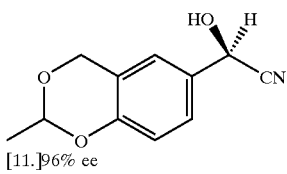

[11.] 96% ee

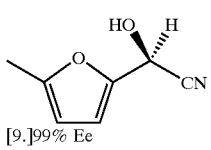

[9.] 99% Ee

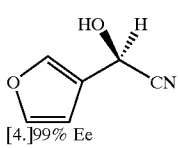

[4.] 99% Ee

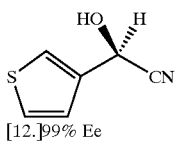

[12.] 99% Ee

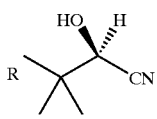

-continued

[5.] 89% ee, R = OH; 96% Ee, R = MeO

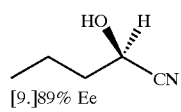

[9.] 89% Ee

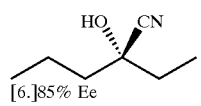

[6.] 85% Ee

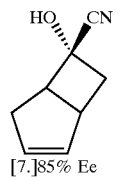

[7.] 85% Ee

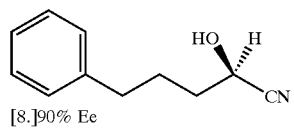

[8.] 90% Ee

[1.] Jastak, J. T.; Yagiela, J. A. J. Am. Dent. Assoc. 1983, 107, 623–630.
[2.] Hondrum, S. O.; Seng, G. E.; Rebert, N. W. Anesthesia and Pain Control in Dentistry 1993, 2, 198–202.
[3.] Madden, J. F.; O'Connor, R. E.; Evens, J. Prehospital Emergency Care 1999, 3, 27–30.
[4.] Venter, D. P. Tetrahedron 1991, 47, 5019–5024.
[5.] Cancañon, F.; Paulus, B. F.; Thompson, G. A.; Ammann, J. R. Investigation of Vasoconstrictor Degradation in Local Anesthetic Injections 30th Annual Meeting & Exhibition of the AADR and 25th Annual Meeting of the CADR, Chicago, 2001.
[6.] Lu, S.; Herbert, B.; Haufe, G.; Laue, K. W.; Padgett, W. L.; Oshunleti, O.; Daly, J. W.; Kirk, K. L. J. Med. Chem. 2000, 43, 1611–1619.
[7.] Kirk, K. L.; Olubajo, O.; Buchhold, K.; Lewandowski, G. A.; Gusowski, F.; McCulloh, D.; Daly, J. W.; Creveling, C. R. J. Med. Chem. 1986, 29, 1982–1988.
[8.] Kirk, K. L. In Selective Fluorination in Organic and Bioorganic Chemistry (Welch, J. T., ed) ACS Symposium Series 456, American Chemical Society: Washington, D.C., 1991, pp. 136–155.
[9.] Zandbergen, P.; van der Linden, J.; Brusse, J.; van der Gen, A. Synth. Commun. 1991, 21, 1387–1391.
[10.] Kiljunen, E.; Kanerva, L. T. Tetrahedron: Asymmetry 1996, 7, 1105–1116.
[11.] Effenberger, F.; Jäger, J. J. Org. Chem. 1997, 62, 3867–3873.
[12.] Effenberger, F.; Eichhom, J. Tetrahedron: Asymmetry (1997) 8, 469–476

Spontaneous (non-enzyme catalyzed) addition of HCN to carbonyl compounds is one of the major problems encountered during PaHNL-catalyzed cyanohydrin synthesis. The optimum of catalytic activity of PaHNL is at pH 5.5. At this pH, the rate of spontaneous HCN addition to most carbonyl compounds is high and negatively affects the optical purity. The rate of enzyme-catalyzed reactions is directly proportional to the enzyme concentration and theoretically the contribution of enzyme-catalyzed reaction can be increased by increasing enzyme concentration. In practice, high enzyme concentration means difficult work-up and difficult (or impossible) enzyme recovery. Both these factors often make the process economically ineffective. As a result, different reaction conditions developed for PaHNL-catalyzed HCN addition (Table 3) mostly focus on the solution of this problem: how to get high rates of PaHNL-catalyzed stereo-selective addition at reasonable enzyme concentrations and avoid spontaneous non-selective cyanohydrin formation.

TABLE 3

Reaction conditions employed in PaHNL-catalyzed synthesis of chiral cyanohydrins. (a) Huuhtanen, T. T.; Kanerva, L. T. Tetrahedron: Asymmetry 1992, 3, 1223–1226; (g) Warmerdam, E. C. J. C.; van der Nieuwendijk, A. M. C. H.; Kruse, C. G.; Brussee, J.; van der Gen, A. Red. Trav. Chim. Pays-Bas 1996, 115, 20–24; (h) Effenberger, F.; Horsch, B.; Weingart, F.; Ziegler, T.; Kuhner, S. Tetrahedron Lett. 1991, 32, 2605–2608; (i) Effenberger, F.; Heid, S. Tetrahedron. Asymmetry 1995, 6, 2945–2952. (a) Schmidt, M.; Griengl, H. In "Biocatalysis-From Discovery to Application" (Fessner, W.-D., ed.), Springer, 1999, pp. 193–226; (b) Brussee, J.; van der Gen, A. In "Stereoselective Biocatalysis" (Patel, R. N., ed.), Marcel Dekker, 2000, pp. 289–320; (c) Effenberger, F. In "Stereoselective Biocatalysis" (Patel, R. N., ed.), Marcel Dekker, 2000, pp. 321–342. Gregory, R. J. H Chem. Rev. 1999, 99, 3649–3682.

| Reaction conditions | Advantages | Disadvantages |
|---|---|---|
| Aqueous media. The reaction is performed at pH between 4 and 5 using in situ generation of HCN from KCN. | The reaction is fast (about 1 hour). Both purified and crude enzyme preparations can be used. The procedure avoids the use of highly toxic free HCN. | The product EE is often low due to uncatalyzed addition of HCN. Immobilized enzyme has a limited application because of low solubility of many aldehydes and ketones. |
| Reaction in water-saturated organic solvents with immobilized enzyme. | Non-catalyzed addition of HCN is almost completely suppressed. Substrate concentration is high due to high solubility of the substrates and products in the reaction media. The use of immobilized enzyme makes possible the enzyme reuse and implement a continuous process. | The use of highly toxic hydrogen cyanide in a neat form is practically unavoidable. In spite of high substrate concentration, the reaction throughput is low because reaction rates are much lower than in aqueous media or biphasic solvent mixtures under the same enzyme loadings. |
| Reaction in biphasic solvent mixtures | Reaction is almost as fast as in pure aqueous media. Uncatalyzed addition of HCN is often suppressed. Reaction throughput is high due to high solubility of the substrates and products in organic phase. The enzyme can be reused by recycling the enzyme aqueous broth. | The enzyme can be reused only if enzyme concentration is low. Otherwise, biphasic solvent mixtures forms stable emulsions. Practically, it requires the use of pure enzyme and limits a large-scale implementation of this method with specific enzyme substrates. |
| Transhydrocyanation in biphasic solvent mixtures (scheme below) | Non-catalyzed addition of HCN is often suppressed. Highly toxic hydrogen cyanide does not have to be used. Reaction throughput is high due to high solubility of the substrates and products in organic phase. | The same as above plus low reaction rates and more complex optimization. |

PaHNL has proven useful in the synthesis of ring-fluorinated cyanohydrins because HCN does not spontaneously add to ortho-fluorinated benzaldehydes to a substantial degree, as demonstrated by our work. Spontaneous addition of HCN to ortho-fluorinated benzaldehydes does not occur because of the low electrophilicity of the carbonyl group caused by the electronegative character of fluorine. Lu, S.; Herbert, B.; Haufe, G.; Laue, K. W.; Padgett, W. L.; Oshunleti, O.; Daly, J. W.; Kirk, K. L. *J. Med. Chem.* 2000, 43, 1611–1619. Certainly, this same factor also lowers the rate of enzyme-catalyzed addition. However, the lower reactivity of ortho-fluorinated benzaldehydes could be compensated for by an increase of enzyme concentration if there were an effective way to recover enzyme and product from concentrated reaction mixtures. Our reversibly soluble biocatalysts focus on a cost-effective solution to this problem.

The reversibly soluble biocatalyst prepared from PaHNL is commercially available in four forms: Finezyme™-H1, Finezyme™-H2, Finezyme™-H3 and Finezyme™-H4. The Finezyme™-H1 and Finezyme™-H2 biocatalysts (Table 4) are made as described in PCT Patent Application No. PCT/US01/28980, entitled "Reversibly Soluble Enzyme-Polymer Conjugates," and the Finezyme™-H3 and Finezyme™-H4 biocatalyst are prepared based on literature precedent using a different enzyme, Arasaratnam, V.; Galaev, I. Y.; Mattiasson, B. *Enz. Microb. Technol.* 2000, 27, 254–263, all of which is incorporated here by reference for a disclosure of how to prepare the enzyme polymer conjugates.

TABLE 4

Properties of Finezyme ™-H series of biocatalysts.

| | Finezyme ™-H1 | Finezyme ™-H2 | Finezyme ™-H3 |
|---|---|---|---|
| Solubility properties | Soluble < 30° C. Insoluble > 35° C. | Soluble < 10° Insoluble > 15° | Soluble at pH > 6.5 Insoluble at pH < 4.5 |
| Protein content (%) | 7 | 8.5 | 4.5 |
| Activity (U/g) | 70 | 300 | 180 |

Commercially available PaHNL sold by Roche Diagnostics as suspension has activity of 580 U/ml of suspension.

Finezyme™ Reversibly Soluble Biocatalysts

Biocatalysis is the most desirable method to produce chiral compounds, because by their nature, enzymes recognize and catalyze reactions producing only one stereoisomer. However, biocatalytic methods are underutilized in industry, due to the necessity for inexpensive work-up and the need for enzyme reuse and high space-time yield (volumetric productivity). Solubility of the compounds is often limited and the latter requirement necessitates running the reactions in heterogeneous systems consisting of the suspension of the starting materials and the products. Free enzymes are active in these systems, but in most cases cannot be reused. Unfortunately, immobilized enzymes have low efficiency in heterogeneous systems.

Figure 14:
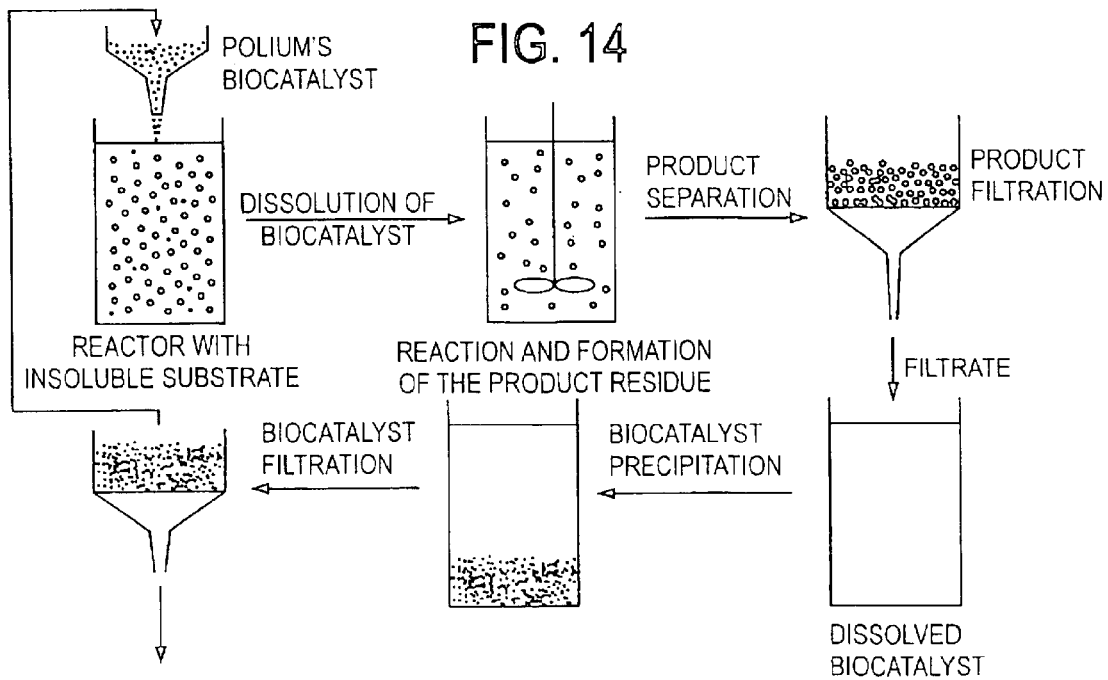
FIG. 14 is a schematic view of a process for using Finezyme™ reversibly soluble biocatalyst for carrying out an enzymatic reaction.

Polium Technologies Finezyme™ reversibly soluble biocatalysts combine the advantages of free and immobilized enzymes. The idea consists in modifying the enzymes with reversibly soluble polymers. These polymers precipitate following a slight change in external conditions. If such a polymer is attached to the enzyme, the biocatalyst can be precipitated without destroying a delicate enzyme structure. Later it can be dissolved again at the initial external conditions. Therefore, reversibly soluble biocatalysts acquire the advantages of free enzymes (high activity in heterogeneous systems) and that of immobilized enzymes and cross-linked enzyme crystals (easy work-up and ability to be reused) (FIG. 14). Easy biocatalyst recovery is not the only advantage of Finezyme™ reversibly soluble biocatalysts. It is equally important that the reversible solubility of Finezyme™ reversibly soluble biocatalysts makes product isolation an easier procedure.

The Use Of Finezyme™ Reversibly Soluble Biocatalysts

Finezyme™-H1 is a co-polymer of PaHNL and poly-N-isopropylacrylamide, Finezyme™-H2 is a co-polymer of PaHNL and poly-(N-isopropylacrylamide-co-N-tert-butylacrylamide), Finezyme™-H3 is a co-polymer of PaHNL and Eudragit® L-100, and Finezyme™-H4 is a co-polymer of PaHNL and Eudragit® S-100. The Eudragit® polymers are available from Röhm America Inc., Piscataway, N.J. The reversible solubility of these biocatalysts allows a scalable method to synthesize the (R)-isomers of fluorinated 6F-epinephrine and phenylephrine.

Polium Technologies Finezyme™-H1 reversibly soluble biocatalyst is used to synthesize 2-methylamino-1R-[(3,4-dihydroxy-6-fluoro)-phenyl]ethanol, [(R)-6F-epinephrine], and 2-methylamino-1R-[(3-hydroxy-6-fluoro)-phenyl] ethanol, [(R)-6F-phenylephrine]. This synthesis is also the first example of the use of biocatalysts for the chiral addition of HCN to ring-fluorinated aldehydes.

Figure 15:
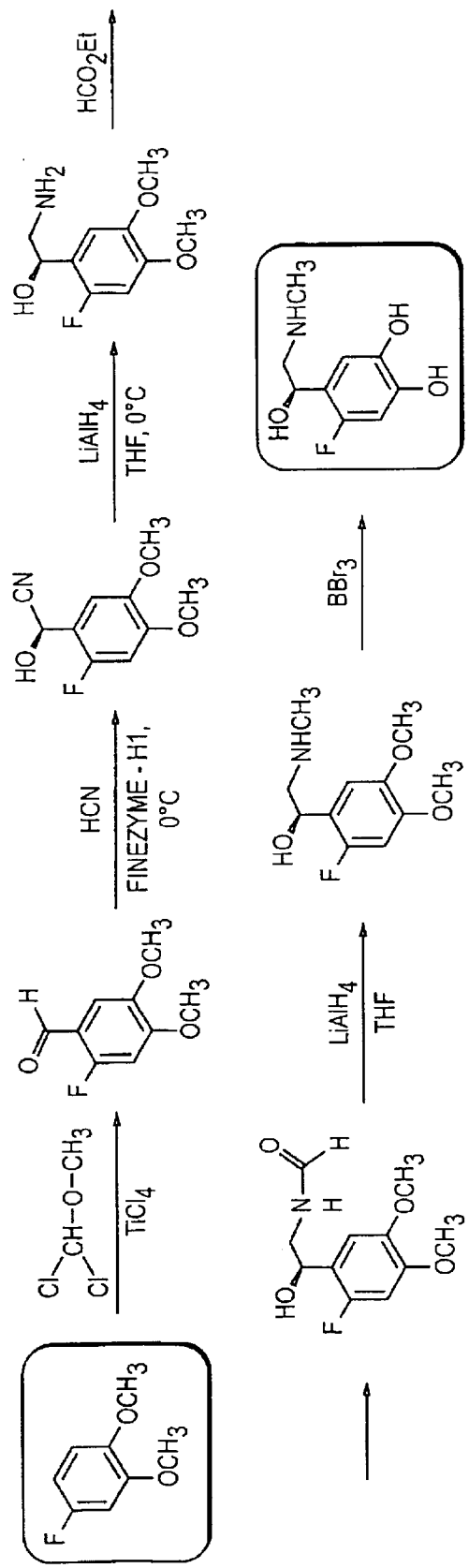
FIG. 15 shows the synthesis of (R)-6F-epinephrine.

Synthesis of both compounds follows similar schemes, starting from different commercially available starting materials. FIG. 15 depicts the synthesis of (R)-6F-epinephrine starting from commercially available 4-fluoroveratrole; the synthesis of (R)-6F-phenylephrine starts from commercially available 2-fluoro-5-methoxybenzaldehyde.

In this context, the specific technical steps can be enumerated as follows:

1) Synthesis of 2-fluoro-4,5-dimethoxybenzaldehyde from 4-fluoroveratrole (FIG. 9)
2) Test activity of almond hydroxynitrile lyase and Finezyme™-H1 with respect to 2-fluoro-5-methoxybenzaldehyde and 2-fluoro-4,5-dimethoxybenzaldehyde
3) Formation of methylated (R)-6F-epinephrine and (R)-6F-phenylephrine by side-chain elaboration
4) Removal of hydroxyl protecting groups Below we describe the procedures used to accomplish these objectives. Procedures used during the accomplishment of technical steps #1 and #3 reproduce respective procedures for (R)-6F-epinephrine. However, we reproduced the literature procedure in its entirety for technical step #1 only. As for technical step #3, modifications of the literature methods were required due to the use of different protecting groups. For this reason, we also developed an original protocol for the removal of the protecting groups. Progress of the reaction was monitored by reverse-phase HPLC on Waters Spherisorb® (5 µM packing) and by thin layer chromatography; optical purity of the products was analyzed on a Cyclobond I 2000 RSP chiral column. Structure of the products was determined by nuclear magnetic resonance.

Synthesis of 2-fluoro-4,5-dimethoxybenzaldehyde

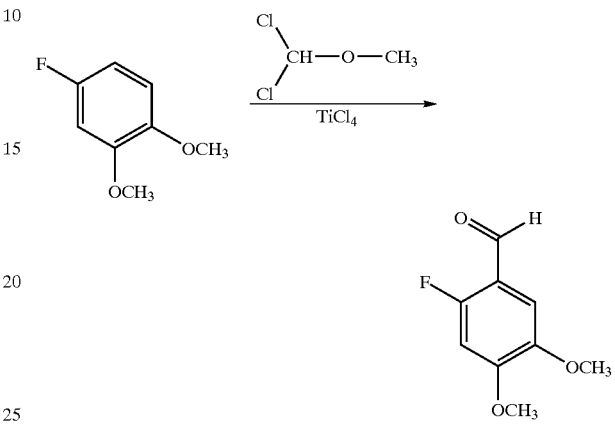

Typical Procedure: Meier, H.; Kretzschmann, H.; Kolshorn, H. *J. Org. Chem.* 1992, 57, 6847–6852. Furlano, D.; Kirk, K. K. *J. Org. Chem.* 1986, 51, 4073–4075.

Figure 16:
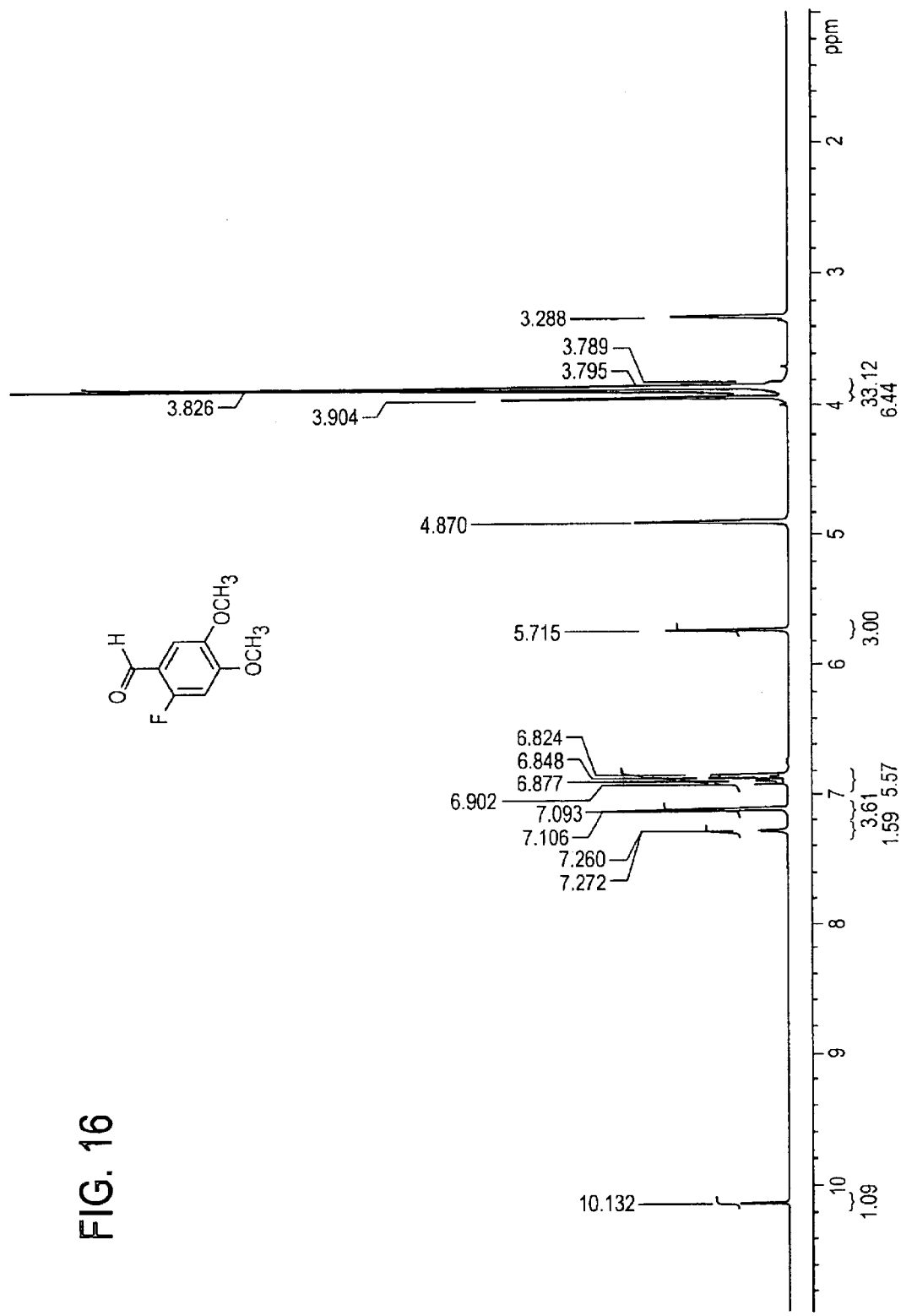
FIG. 16 shows the NMR plot of 2-fluoro-4,5-dimethoxybenzaldehyde.

To a chilled solution (0° C.) of 1.0 g (6.4 mmol) of 4-fluoroveratrole in 6.5 mL anhydrous dichloromethane was added 10.5 mL of 1.0 M titanium (IV) chloride (10.5 mmol; in $CH_2Cl_2$), over 30 m and under inert atmosphere. Following this, a solution of 0.826 g (7.2 mmol) of dichloromethyl methyl ether in 2.0 mL anhydrous dichloromethane slowly was added to the reaction. After this addition was complete, the ice bath was removed and the reaction stirred at room temperature for an additional 3 h. The reaction then was poured over 25 g crushed ice, and extracted with ether (3×20 mL). The combined organic layers were washed with saturated sodium bicarbonate (3×20 mL) and with brine (1×20 mL), dried over sodium sulfate, and evaporated under reduced pressure. The product was purified using flash chromatography with 15% ethyl acetate in hexanes. The product gave the NMR shown in FIG. 16.

Enzyme-catalyzed HCN Addition

The procedure differs from a typical literature method Schmidt, M.; Herve, S.; Klempier, N.; Griengl, H. *Tetrahedron* 1993, 34, 7833–7836, respecting the pH of the reaction media. The low electrophilicity of the carbonyl group in ring-fluorinated benzaldehydes allows the enzyme-catalyzed HCN addition to be performed at pH ~5.5. At this pH, almond hydroxynitrile lyase shows highest activity and stability. The following reactions were performed using both the R- and S-oxynitrilase and the R- and S-Finezyme™-H1 prepared from the enzymes.

Typical Procedure

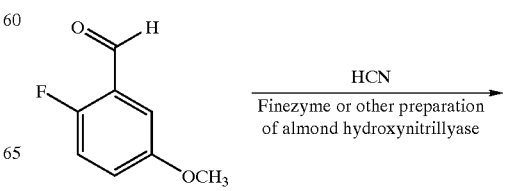

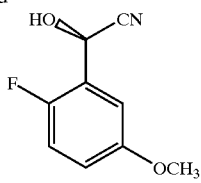

Enzyme-catalyzed synthesis of 2-fluoro-5-methoxyphenyl-hydroxy-acetonitrile and 2-fluoro-4,5-methoxyphenyl-hydroxyl-acetonitrile

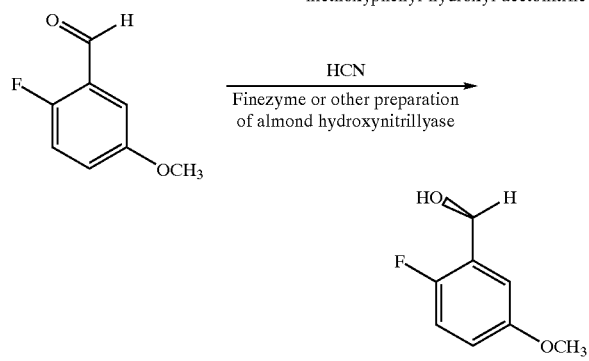

Below we describe the synthesis of mono-methoxy cyanohydrin in gram amounts. The dimethoxy derivative was synthesized using a similar procedure.

Figure 17:
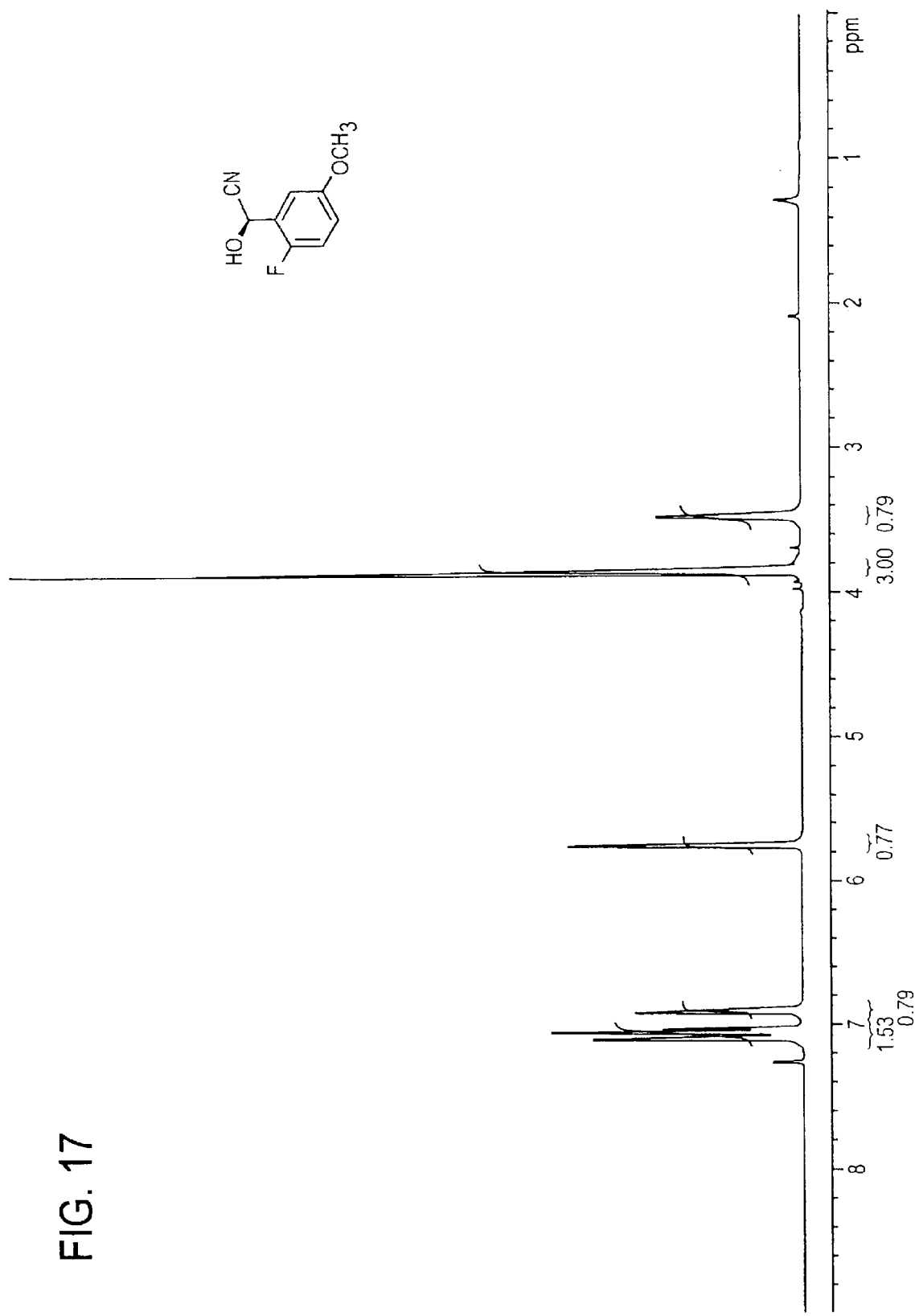
FIG. 17 shows the NMR plot of monomethoxycyanohydrin.
Figure 18:
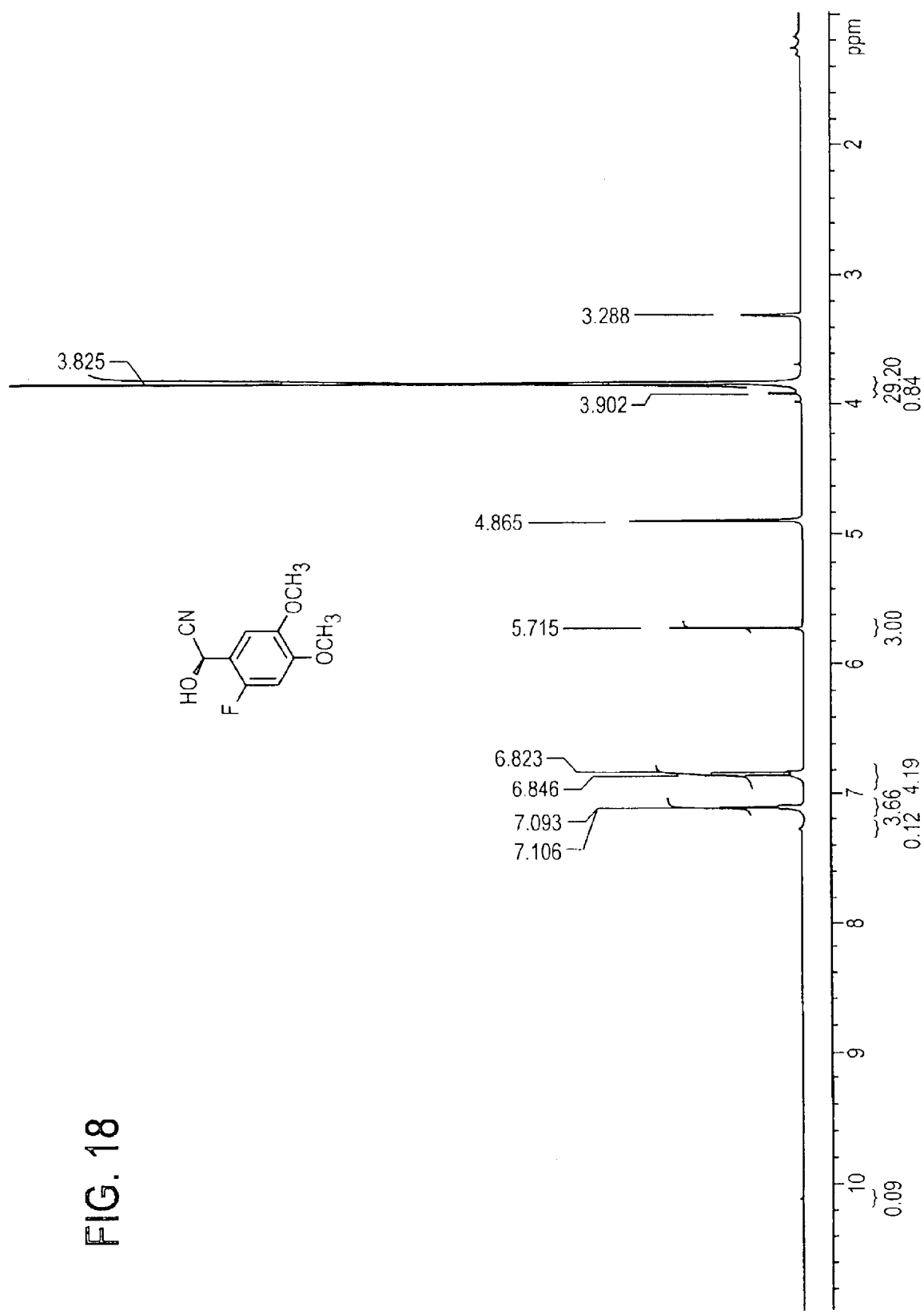
FIG. 18 shows the NMR plot of dimethoxycyanohydrin.

To 5.0 g (32.4 mmol) of 2-fluoro-5-methoxybenzaldehyde in 40 mL $H_2O$:ethanol (1:1) was added 1100 units of Finezyme™-H1 biocatalyst (or ~780 units of (R)-Oxynitrilase, grade III; Biocatalytics) and the mixture was chilled in an ice water bath. A chilled solution (0° C.) of 1 N KCN/HOAc buffer (pH 5.4) in ethanol (60 mL KCN/HOAc in 20 mL ethanol) was added to the aldehyde over 1 h. The reaction was stirred for 30 m after the addition was complete, then was extracted with ether (3×100 mL). The combined organic layers were washed with 10% NaCl (3×75 mL), dried over sodium sulfate and evaporated under reduced pressure. The product was crystallized from dichloromethane and hexanes. The NMR spectra of FIGS. 17 and 18 were obtained for the mono-methoxy and dimethoxy cyanohydrins, respectively.

Side-chain Elaboration (Similar Methodologies Used to Reach Both (R)-6F-Phenylephrine and (R)-6F-epinephrine)

a. Reduction of 2-fluoro-5-methoxyphenyl-hydroxy-acetonitrile to 2-amino-2R-(2-fluoro-5-methoxy-phenyl)-ethanol The method described below is based on the procedure developed for benzyloxy-protected cyanohydrins. Lu, S.; Herbert, B.; Haufe, G.; Laue, K. W.; Padgett, W. L.; Oshunleti, O.; Daly, J. W.; Kirk, K. L. *J. Med. Chem.* 2000, 43, 1611–1619.

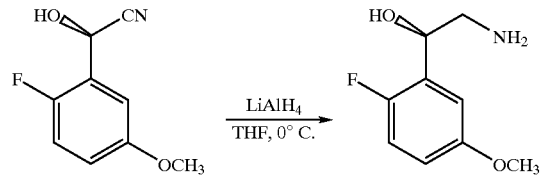

Figure 19:
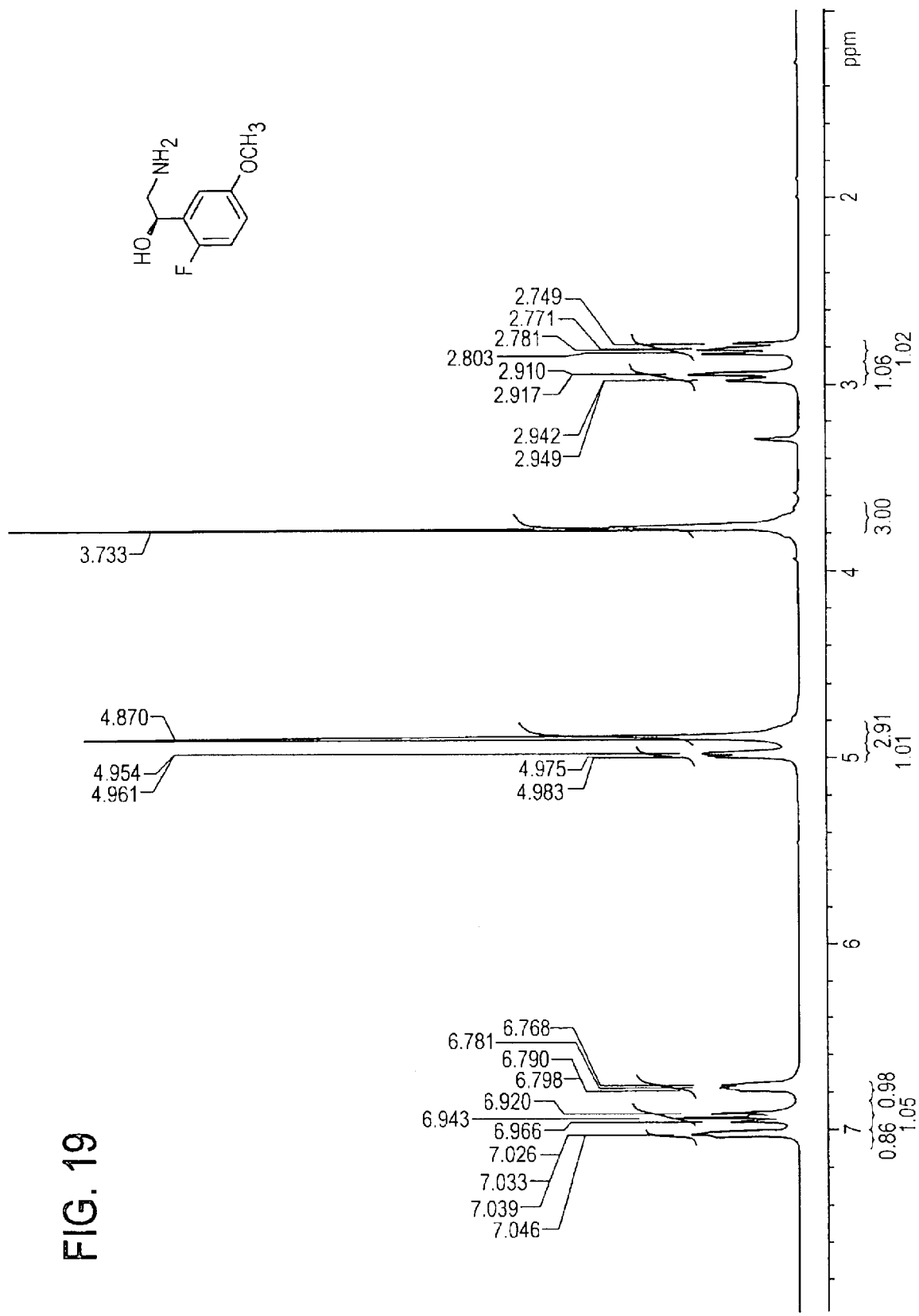
FIG. 19 shows the NMR plot of 2-amino-2R-(2-fluoro-5-methoxyphenyl)ethanol.

To a chilled suspension (0° C.) of 0.90 g (24 mmol) of lithium aluminum hydride in 120 mL THF (under inert atmosphere) was added 2.0 g (11 mmol) of 2-fluoro-5-methoxyphenyl-hydroxy-acetonitrile in 120 mL THF. Following the addition, the reaction was stirred at 0° C. for 20 m, then stirred at ambient temperature for an additional 3 h. 25 mL of water then was added to the reaction mixture, and the organics separated. The water was back extracted with ether (2×50 mL), and the combined organic layers were washed with brine (3×50 mL) and evaporated under reduced pressure. The product was purified using flash chromatography (gradient of 10–30% methanol in dichloromethane). The NMR spectrum of FIG. 19 was obtained.

b. Synthesis of N-[2-(2-fluoro-5-methoxy-phenyl)-2R-hydroxyethyl]-formamide Brown, H. C.; Brady, J. D. *J. Am. Chem. Soc.* 1952, 74, 3570–3576.

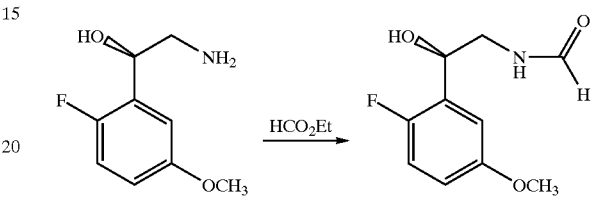

Figure 20:
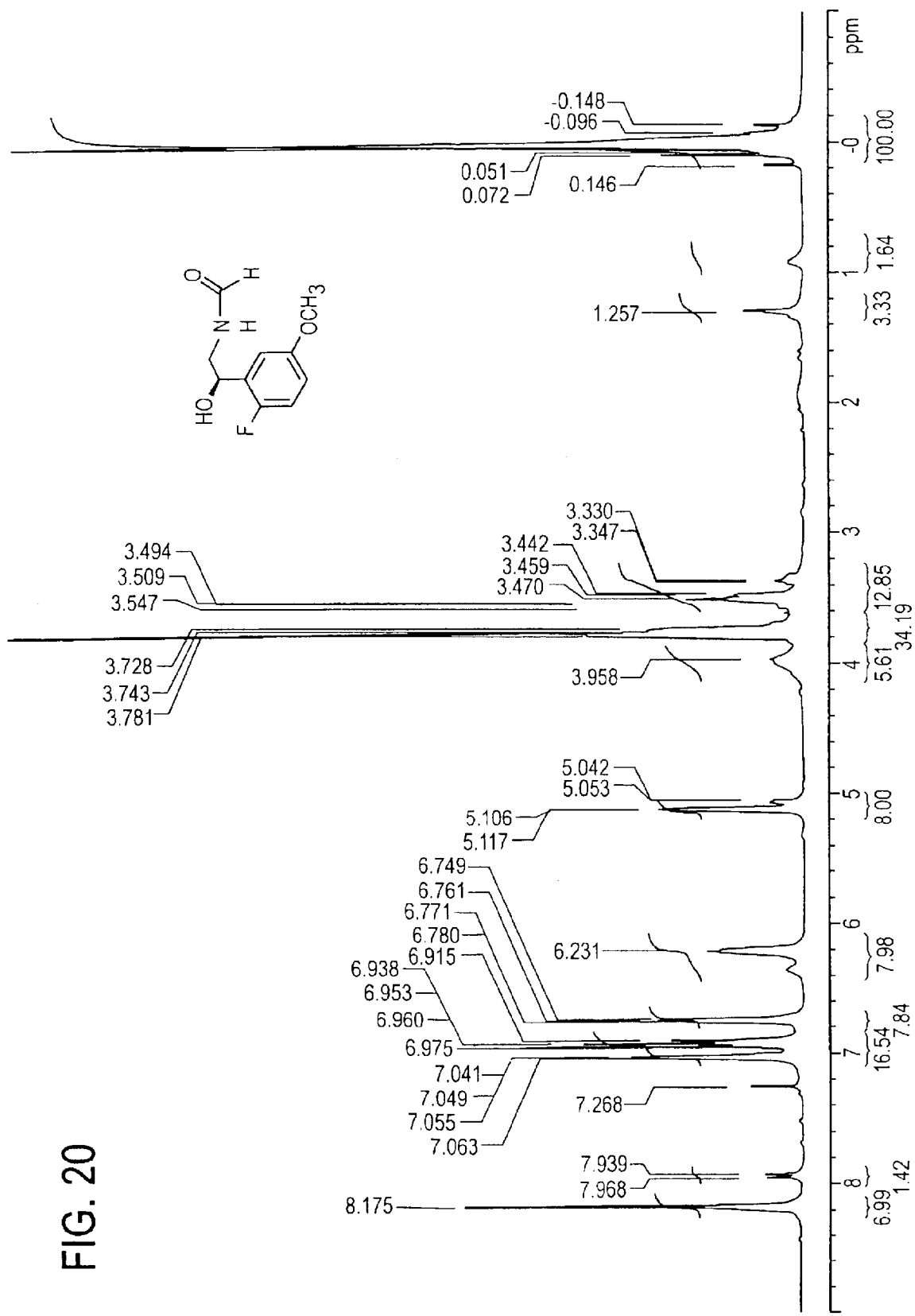
FIG. 20 shows the NMR plot of N-[2-(2-fluoro-5-methoxyphenyl)-2R-hydroxy-ethyl]formamide.

A solution of 2-amino-2R-(2-fluoro-5-methoxy-phenyl)-ethanol (0.5 g, 2.5 mmol) in ethyl formate (30 mL), under inert atmosphere, was heaied to reflux (~60° C.). The reaction was stirred for 4 h, then 30 mL ethyl acetate was added and the reaction was washed with water (40 mL) and brine (2×50 mL). The organics were separated and then dried in vacuo. The NMR spectrum of FIG. 20 was obtained.

c. Reduction of N-[2-(2-fluoro-5-methoxy-phenyl)-2R-hydroxyethyl]-formamide to 1-(2-fluoro-5-methoxy-phenyl)-2-methylamino-ethanol Brown, H. C.; Brady, J. D. *J. Am. Chem. Soc.* 1952, 74, 3570–3576.

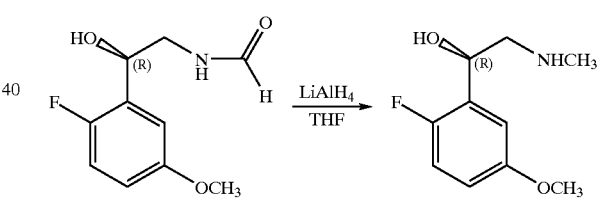

Figure 21:
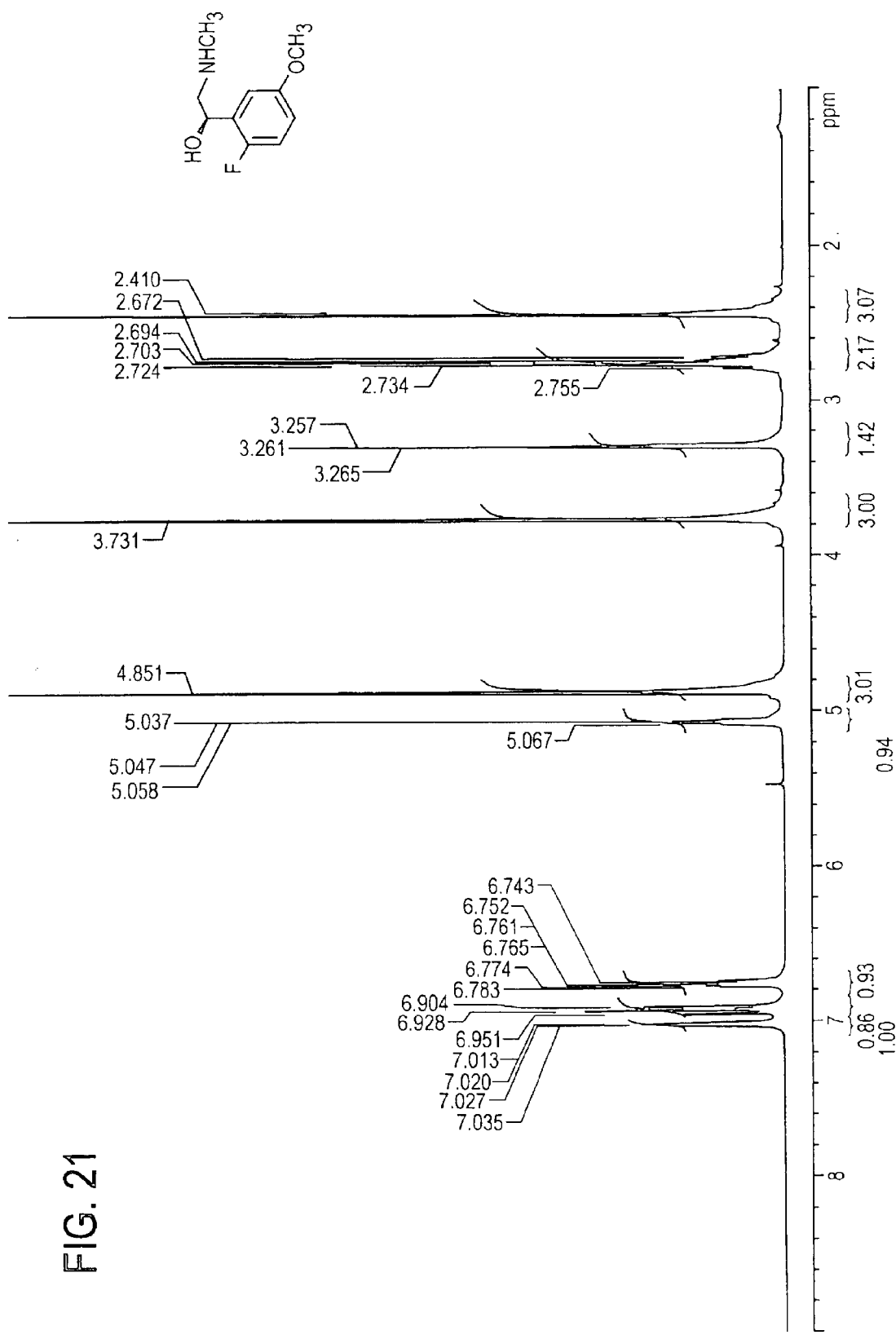
FIG. 21 shows the NMR plot of 1-(2-fluoro-5-methoxyphenyl)-2-methylaminoethanol.

To a chilled suspension (0° C.) of 0.35 g (9.3 mmol) of lithium aluminum hydride in 15 mL anhydrous THF was added slowly 0.80 g (3.8 mmol) of N-[2-(2-fluoro-5-methoxy-phenyl)-2R-hydroxyethyl]-formamide in 40 mL THF (under inert atmosphere). Following the addition, the reaction was stirred at 0° C. for 20 m, then stirred at ambient temperature for an additional 2 h. 75 mL of water then was added to the reaction mixture, and the organics separated. The water was back extracted with ether (2×50 mL), and the combined organic layers were washed with brine (3×50 mL), dried over sodium sulfate and evaporated under reduced pressure. The product was purified using flash chromatography (25% methanol in dichloromethane). The NMR spectrum of FIG. 21 was obtained.

Protecting Group Removal Markovich, K. M.; Tantishaiyakul, Hamada, A.; Miller, D. D.; Romstedt, K. J.; Shams, G.; Shin, Y.; Fraundorfer, P. F.; Doyle, K.; Feller D. R. *J. Med. Chem.* 1992, 35, 466–479.

Synthesis of 4-fluoro-3-(1-hydroxy-2-methylamino-ethyl)-phenol, also Referred to as (R)-6F-phenylephrine

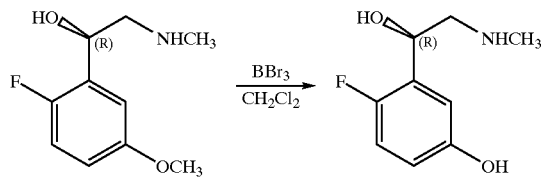
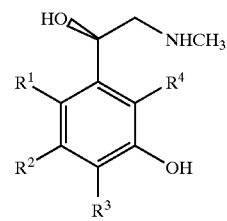

Figure 22:
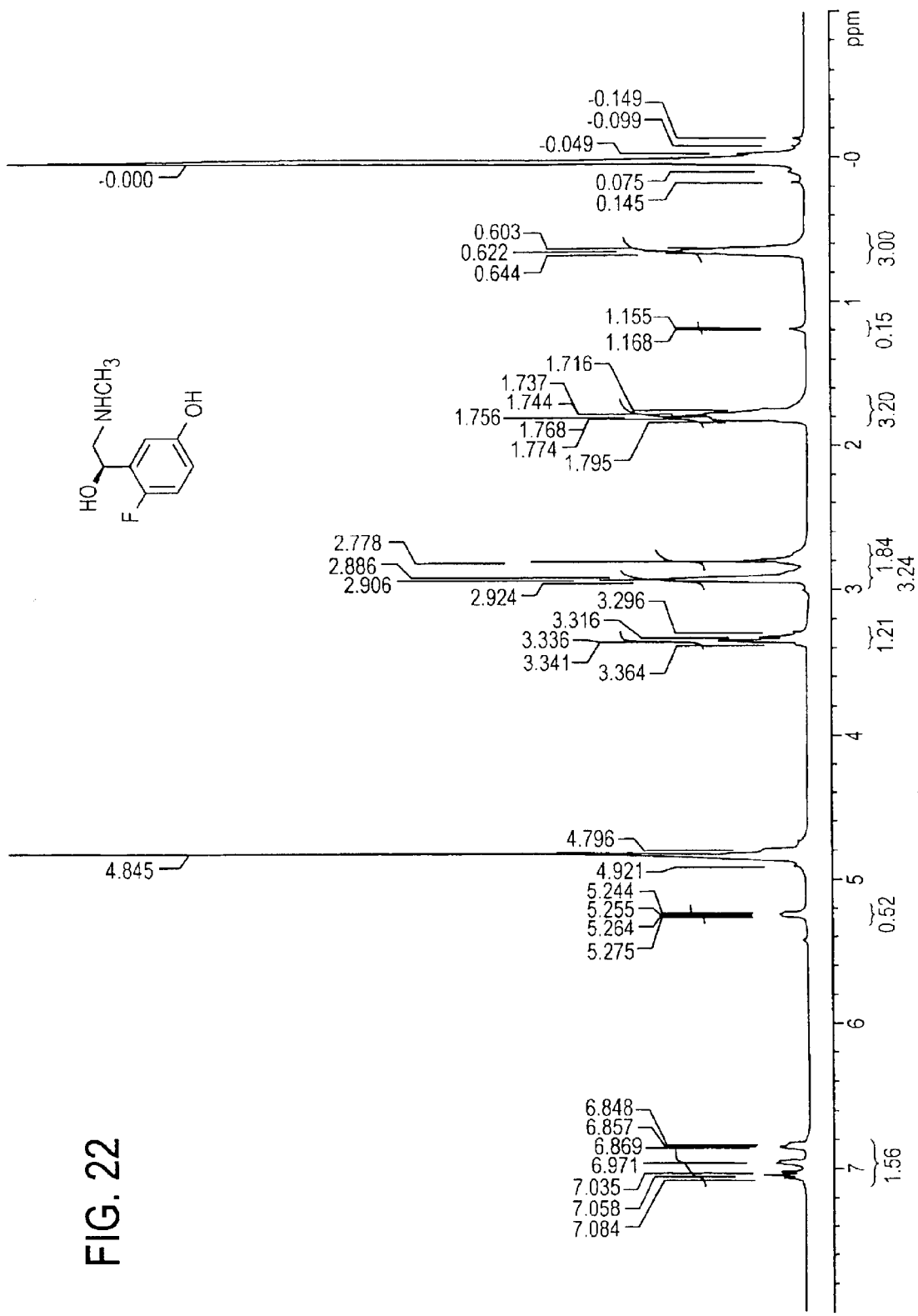
FIG. 22 shows the NMR plot of (R)-6F-phenylephrine.

To a cooled solution (0° C.) of 1-(2-fluoro-5-methoxy-phenyl)-2-methylamino-ethanol (0.37 g, 2.0 mmol) in 35 mL dichloromethane (under $N_2$) was added 1.0 M boron tribromide in dichloromethane (6 mL, 6.0 mmol). The reaction was stirred at ambient temperature for ~24 h, then 20 mL ethyl acetate was added, and the aqueous layer separated and dried by lyophilization. The contents of the aqueous layer were analyzed by HPLC using a chiral column to determine chiral purity. The NMR spectrum of the product obtained is shown in FIG. 22.

General Synthetic Method

The chiral addition step in the above syntheses can be generalized as a method of chiral addition of cyanide to a ring-fluorinated phenaldehyde, comprising the steps of:

Providing a ring-fluorinated phenaldehyde; and

Reacting said ring-fluorinated phenaldehyde with a source of cyanide in the presence of a catalytic amount of a hydroxynitrile lyase enzyme, thereby forming a ring-fluorinated 1R-cyanohydrin.

The ring-fluorinated cyanohydrin and hydroxynitrile lyase enzyme in the form of a reversibly soluble polymer conjugate can be separated by precipitating and filtering out the product while the enzyme conjugate is maintained in its soluble state, then recovering at least a substantial portion of the almond hydroxynitrillyase enzyme in a form suitable for re-use in said reaction by insolubilizing the enzyme, as by adjusting the pH of the solution, and filtering. The steps of precipitating and removing the product and precipitating and removing the enzyme conjugate can also be reversed, particularly if the product can be maintained in a soluble form while insolubilizing and removing the enzyme. The at least substantial portion of the enzyme recovered can be at least 20%, alternatively at least 30%, alternatively at least 40%, alternatively at least 50%, alternatively at least 60%, alternatively at least 70%, alternatively at least 80%, altomaively at least 90% of the enzyme. 100% recovery of the enzyme would be ideal.

Anesthetic Formulations

The local anesthetic formulations contemplated here are analogous to preexisting formulations containing an anesthetic agent and a vasoconstrictor, but containing the new fluorinated, essentially (R)-chiral analogs of epinephrine and phenylephrine defined above. One example of such a formulation is a composition comprising:

an amount of an anesthetic effective to provide local anesthetic activity;

an amount of an (R)-chiral compound having the structure:

wherein $R^1$, $R^2$, $R^3$, and $R^4$ are independently selected from —H or —F, and at least one of $R^1$, $R^2$, $R^3$, and $R^4$ is —F, essentially free of the (S)-chiral form, or a pharmaceutically acceptable salt or ester thereof, effective to provide vasoconstrictive activity.

In alternative formulations, the anesthetic agent can be, for example, lidocaine or a pharmaceutically acceptable salt or ester, such as the hydrochloride salt. Additionally, any of the conventionally used anesthetic agents can be used in place of some or all of the lidocaine. Such other local anesthetics include benzocaine, dyclonine, pramoxine, etidocaine, mepivacaine, chloroprocaine, procaine, bupivacaine, levobupivacaine, ropivacaine and the like.

In alternative formulations, the vasoconstrictor can be (R)-6F-phenylephrin, (R)-6F-epinephrin, or combinations thereof or a pharmaceutically acceptable salt or ester, such as the bitartrate salt. Other vasoconstrictors known for use in local anesthetic formulations optionally can be used as well. Examples are ephedrine, pseudoephedrine and the like.

The term "pharmaceutically acceptable salt" refers to a salt prepared from a base or acid that is acceptable for administration to a patient, such as a mammal. Such salts can be derived from pharmaceutically acceptable inorganic or organic bases and from pharmaceutically acceptable inorganic or organic acids. Salts derived from pharmaceutically acceptable inorganic bases include aluminum, ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, fumaric, gluconic, glucoronic, glutamic, hippuric, hydrobromic, hydrochloric, isethionic, lactic, lactobionic, maple, malic, mandelic, methanesulfonic, mucic, naphthalenesulfonic, nicotinic, nitric, pamoic, pantothenic, phosphoric, succinic, sulfuiric, tartaric (providing a tartrate or bitartrate), p-toluenesulfonic and the like. Particularly preferred are citric, hydrobromic, hydrochloric, maple, phosphoric, sulfuric and tartaric acids.

The anesthetic agent can be present as at least 0.1% by weight, alternatively at least 0.5% by weight, alternatively at least 1% by weight of the composition. The anesthetic agent can be present as at most 10%, alternatively at most 5%, alternatively at most 3% by weight of the composition.

The vasoconstrictor can be present at a ratio of at most 1:10,000 (1 g by weight per 100,000 mL of the composition), alternatively at most 1:25,000, alternatively at most 1:50,000, alternatively at most 1:75,000, alternatively at most 1:100,000. The vasoconstrictor can be present at a ratio of at least 1:500,000, alternatively at least 1:200,000, alternatively at least 1:100,000.

The inventors contemplate that any conventional adjuvants can be used in the present composition. These may include antioxidants, for example sodium or potassium metabisulfite; isotonic agents such as sodium chloride; chelating agents such as EDTA or citric acid; pH adjustment agents such HCl or NaOH, present in an amount desirable to achieve a pH of, for example, from 3.3–5.5; minor impurities such as aluminum salts; and other ingredients. Other adjuvants that may find use herein include opiates, such as morphine and fentanyl (used to provide epidural/spinal anesthesia); NMDA antagonists, such as dextromethorphan; clonidine; antiinflammatory agents; antibiotics; and the like. When preparing the pharmaceutical compositions of this invention, the active ingredient is customarily diluted by an excipient. Representative examples of suitable excipients include water, sterile saline, syrup, and methyl cellulose. The formulations can additionally include emulsifying and suspending agents; preserving agents, such as methyl- and propylhydroxy-benzoates; and flavoring and coloring agents.

The compounds of this invention may be formulated using conventional techniques such as those described in Remington's Pharmaceutical Sciences, Mace Publishing Co., Philadelphia, Pa. 17th Ed. (1985) and "Modern Pharmaceutics," Marcel Dekker, Inc. 3.sup.rd Ed. (G. S. Banker & C. T. Rhodes, Eds.). Pharmaceutically acceptable salts of the active agents (e.g., acid addition salts) may be prepared using standard procedures known to those skilled in the art of synthetic organic chemistry and described, e.g., by J. March, Advanced Organic Chemistry: Reactions, Mechanisms and Structure, 4th Ed. (New York: Wiley-Interscience, 1992).

The compounds may be administered by any of the accepted modes of administration for agents having similar utilities, for example, by oral, topical, parenteral (e.g., intradermal, intravenous, subcutaneous, intramuscular), intra-articular, intraspinal, epidural, rectal, vaginal, or transdermal/transmucosal routes. The most suitable route will depend on the nature and severity of the condition being treated and will be determined by a physician. Subcutaneous, intradermal and percutaneous injections (intended to deliver the agent in close proximity to a peripheral nerve trunk) are preferred routes of administration for the compounds of this invention.

For topical use, the pharmaceutical compositions can be in the form of emulsions, creams, jellies, solutions, or ointments containing, for example, up to 5% by weight of the active compound.

For parenteral administration, the pharmaceutical compositions can be in the form of sterile injectable solutions and sterile packaged powders. Preferably, injectable solutions are formulated at a pH of 4.5±0.3.

The pharmaceutical compositions of the invention can also be formulated so as to provide quick, sustained or delayed release of the active ingredient after administration to, the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543–551 (1997), all of which are incorporated herein by reference.

Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252; 5,719,197; and 4,992,445, all of which are incorporated herein by reference. Such patches may be constructed for continuous, pulsatile, or on demand delivery of pharmaceutical agents.

The pharmaceutical compositions are preferably formulated in a unit dosage form. The term "unit dosage forms" refers to physically discrete units suitable as unitary dosages for human subjects and other mammals, each unit containing a predetermined quantity of active material calculated to produce the desired anesthetic effect in association with a suitable pharmaceutical excipient (e.g., provided in an ampoule).

The compounds of this invention are typically administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like. Suitable doses for producing local anesthesia in a mammal range from about 5 mg to about 1000 mg per dose.

What is claimed is:

1. (R)-6F-phenylephrine, essentially free of (S)-6F-phenylephrine.

2. An anesthetic formulation comprising said (R)-6F-phenylephrine of claim 1 or a pharmaceutically acceptable salt or ester therof, and having improved stability compared to formulations containing their non-flourinated analogs.

3. A method of providing vasoconstriction in a mammal, comprising the step of administering to said mammal an amount of said (R)-6F-phenylephrine of claim 1 or a pharmaceutically acceptabler salt or ester thereof effective to provide vasoconstricting activity.

4. A composition comprising:
   an amount of an anesthetic effective to provide local anesthetic activity; and
   an amount of said (R)-6F-phenylephrine of claim 1 or a pharmaceutically acceptable salt or ester thereof, effective to provide vasoconstrictive avtivity.

5. A local anesthetic composition comprising:
   from 0.1% to 20% by weight of an anesthetic agent;
   from 0.0001% to 0.01% of a vasoconstrictor comprising said (R)-6F-phenylephrine of claim 1 or a pharmaceutically acceptable salt or ester thereof; and
   as the balance, adjuvants and an excipient in a predominant quantity.

6. The composition of claim 4, wherein said anesthetic agent is lidocaine hydrochloride.

7. The local anesthetic composition of claim 5, wherein said anesthetic agent is lidocaine hydrochloride.

* * * * *